(12) United States Patent
Wickens

(10) Patent No.: US 11,395,839 B2
(45) Date of Patent: Jul. 26, 2022

(54) USE OF LACTIC ACID BACTERIA TO TREAT OR PREVENT GESTATIONAL DIABETES MELLITUS

(71) Applicant: UNIVERSITY OF OTAGO, Dunedin (NZ)

(72) Inventor: Kristin Lee Wickens, Wellington (NZ)

(73) Assignee: University of Otago, Dunedin (NZ)

( * ) Notice: Subject to any disclaimer, the term of this patent is extended or adjusted under 35 U.S.C. 154(b) by 118 days.

(21) Appl. No.: 16/472,071

(22) PCT Filed: Jun. 2, 2017

(86) PCT No.: PCT/IB2017/053262
§ 371 (c)(1),
(2) Date: Jun. 20, 2019

(87) PCT Pub. No.: WO2018/115985
PCT Pub. Date: Jun. 28, 2018

(65) Prior Publication Data
US 2020/0093873 A1 Mar. 26, 2020

(30) Foreign Application Priority Data

Dec. 22, 2016 (NZ) ........................ 727914

(51) Int. Cl.
| | | |
|---|---|---|
| A61K 35/747 | (2015.01) | |
| A61K 39/00 | (2006.01) | |
| A61P 3/10 | (2006.01) | |
| A61K 9/00 | (2006.01) | |

(52) U.S. Cl.
CPC .......... *A61K 35/747* (2013.01); *A61K 9/0056* (2013.01); *A61P 3/10* (2018.01); *A61K 2039/521* (2013.01); *A61K 2039/522* (2013.01)

(58) Field of Classification Search
None
See application file for complete search history.

(56) References Cited

U.S. PATENT DOCUMENTS

| | | | |
|---|---|---|---|
| 9,737,575 B2 * | 8/2017 | Crane ................ | A61K 35/747 |
| 2011/0177044 A1 | 7/2011 | Thomas et al. | |
| 2012/0045422 A1 * | 2/2012 | Crane ................ | A61K 45/06 |
| | | | 424/93.45 |

FOREIGN PATENT DOCUMENTS

| | | |
|---|---|---|
| RU | 2208632 C2 | 7/2003 |
| WO | WO 1999/010476 | 3/1999 |
| WO | WO 2010/064930 | 6/2010 |
| WO | WO 2016/198528 | 12/2016 |

OTHER PUBLICATIONS

Kumar et al. J. Allerg. Clin. Immunol. 124: 1031-1038, 2009.*
ANZCTR—Australian New Zealand Clinical Trials Registry, pp. 1-5, Jul. 16, 2016.*
Ahmed et al.Effects of probiotics (*Lactobacillus rhamnosus*) in reducing glucose intolerance during and after pregnancy: a double blind randomized controlled trial in antenatal clinic of Karachi-Pakistan (GRIP), http://clinicaltrails.gov/show/NCT014364, accessed Jul. 6, 2012, pp. 1/8 to 8/8.*
ANZCTR Trial Review, pp. 1-12, Feb. 7, 2012.*
International Search Report and Written Opinion in PCT/IB2017/053262 dated Aug. 18, 2017 in 10 pages.
Barthow, C. et al. "The Probiotics in Pregnancy Study (PiP Study): rationale and design of a doubleblind randomised controlled trial to improve maternal health during pregnancy and prevent infant eczema and allergy" BMC Pregnancy and Childbirth (Jun. 3, 2016) vol. 16, No. 133, pp. 1 to 14.
Barrett, H.L. et al. "Probiotics for preventing gestational diabetes (Review)" Cochrane Database of Systematic Reviews (2014), Issue 2, Article No. CD009951, DOI: 10.1002/14651858.CD009951.pub2.
Ministry of Health (2014) Screening, diagnosis and management of gestational diabetes in New Zealand: A clinical practice guideline. Ministry of Health, Wellington.
Kim SY, England L, Wilson HG, Bish C, Satten GA, Dietz P (2010) Percentage of gestational diabetes mellitus attributable to overweight and obesity. Am J Pub Health 100: 1047-1052.
Ben-Haroush A, Yogev Y, Hod M (2004) Epidemiology of gestational diabetes mellitus and its association with Type 2 diabetes. Diabet Med 21: 103-113.
Kim C, Newton KM, Knopp RH (2002) Gestational diabetes and the incidence of type 2 diabetes. Diabetes Care 25: 1862-1868.
International Association of Diabetes and Pregnancy Study Groups Consensus Panel (2010) International Association of Diabetes and Pregnancy Study Groups Recommendations on the diagnosis and classification of hyperglycemia in pregnancy. Diabetes Care 33: 676/682.
Luoto R, Laitinen K, Nermes M, Isolauri E (2010) Impact of maternal probiotic-supplemented dietary counselling on pregnancy outcome and prenatal and postnatal growth: a double-blind, placebo-controlled study. Br J Nutr 103: 1792-1799.
Wickens K, Black PN, Stanley TV, et al. (2008) A differential effect of 2 probiotics in the prevention of eczema and atopy: a double-blind, randomized, placebo-controlled trial. J Allergy Clin Imunol 122: 788-794.
Koren O, Goodrich JK, Tyler CC, et al. (2012) Host remodelling of the gut microbiome and metabolic changes during pregnancy. Cell 150: 470-480.
Barrett HL, Dekker Nitert M, Conwell LS, Callaway LK. Probiotics for preventing gestational diabetes. Cochrane Database Syst Rev. 2014; Art. No. CD00951. DOI: 10.1002/14651858.CD009951.

(Continued)

*Primary Examiner* — Sarvamangala Devi
(74) *Attorney, Agent, or Firm* — Knobbe, Martens, Olson & Bear, LLP

(57) ABSTRACT

The present invention provides methods of treating or preventing gestational diabetes by administering *Lactobacillus rhamnosus* HN001 or derivatives thereof, in addition to uses, compositions, and medicaments comprising *Lactobacillus rhamnosus* HN001 or derivatives thereof to treat or prevent gestational diabetes mellitus.

18 Claims, 3 Drawing Sheets

(56) References Cited

OTHER PUBLICATIONS

Poston L, Harthoorn LF, Van Der Beek EM. Obesity in pregnancy: Implications for the mother and lifelong health of the child. A consensus statement. Pediatr Res. 2011; 69:175-80.

Vohr BR, Boney CM. Gestational diabetes: the forerunner for the development of maternal and childhood obesity and metabolic syndrome? J Matern Neonatal Med. 2008; 21:149/57.

Chandler-Laney PC, Bush NC, Granger WM, Rouse DJ, Mancuso MS, Gower BA. Overweight status and intrauterine exposure to gestational diabetes are associated with children's metabolic health. Pediatr Obes. 2011; 7:44-52.

Nitert MD, Barrett HL, Foxcroft K, Tremellen A, Wilkinson S, Lingwood B, et al. SPRING: an RCT study of probiotics in the prevention of gestational diabetes mellitus in overweight and obese women. BMC Pregnancy Childbirth. 2013; 13:50.

Sung V, Hiscock H, Tang M, Mensah F, Nation M, Satzke C, et al. (2014): Treating infant colic with the probiotic Lactobacillus reuteri: double blind placebo controlled randomised trial. BMJ 348: 2107.

Aaltonen, J, Ojala, T, Laitinen, K, Poussa, T, Ozanne, S, Isolauri, E (2011): Impact of maternal diet during pregnancy and breastfeeding on infant metabolic programming: a prospective randomized controlled study. European Journal of Clinical Nutrition 65: 10-19.

Coustan DR, Lower LP, Metzger BE, Dyer AR (2010) The Hyperglycemia and Adverse Pregnancy Outcome (HAPO) study: paving the way for new diagnostic criteria for gestational diabetes mellitus. Am J Obstet Gynecol 202: 654.e651-e656.

Food and Agriculture Organization/World Health Organization (2002) Guidelines for the evaluation of probiotics in food. Report of a joint FAO/WHO Working Group on drafting guidelines for the evaluation of probiotics in food. Ontario, Canada.

Gomes AC, Beuno AA, de Souza RGM, Mota JF (2014) Gut microbiota, probiotics and diabetes. Nutr J 13 10.1186/1475-2891-13-60.

Zhang Q, Yucheng W, Xiaoqiang F (2016) Effect of probiotics on glucose metabolism in patients with type 2 diabetes mellitus; A meta-analysis of randomized controlled trials. Medicina 52: 28-34.

Thomas LV, Ockhuizen T, Suzuki K (2014) Exploring the influence of the gut microbiota and probiotics on health: a symposium report. Br J Nutr 112: S1-S18. doi:10.1017/S0007114514001275.

Laitinen K, Poussa T, Isolauri E, and the Nutrition, Allergy, Mucosal Immunology and Intestinal Microbiotia Group (2009) Probiotics and dietary counselling contribute to glucose regulation during and after pregnancy: a randomized controlled trial. Br J Nutr 101: 1679-1687.

Lindsay KL, Kennelly M, Culliton M, et al. (2014) Probiotics in obese pregnancy do not reduce maternal fasting glucose: a double-blind, placebo-controlled, randomized trial (Probiotics in Pregnancy Study). Am J Clin Nutr 99: 1432-1439.

Lindsay KL, Brennan L, Kennelly MA, et al. (2015) Impact of probiotics in women with gestational diabetes mellitus on metabolic health: a randomized controlled trial. Am J Obstet Gynecol 212: 496.e491.

Francino MP (2016) Antibiotics and the human gut microbiome: dysbiosis and accumulation of resistances. Front Microbiol 6: 1543. 10.3389/fmicb.2015.01543.

Prescott SL (2013) Early-life environmental determinants of allergic diseases and the wider pandemic of inflammatory noncommunicable diseases. J Allergy Clin Immunol 131: 23-30.

Fattah C, Farah N, Barry SC, O'Connor N, Stuart B, Turner MJ (2010) Maternal weight and body composition in the first trimester of pregnancy. Acta Obstet Gynecol Scand 89: 952-955.

Bravo, JA, Forsythe, P, Chew, MV, Escaravage, E, Savignac, HM, Dinan, TG, Bienenstock, J, Cryan, JF (2011): Ingestion of Lactobacillus strain regulates emotional behavior and central GABA receptor expression in a mouse via the vagus nerve. PNAS 108: 16050-16055.

Zheng et al., "A taxonomic note on the genus *Lactobacillus*: Description of 23 novel genera, emended description of the genus *Lactobacillus* Beijerinck 1901, and union of *Lactobacillaceae* and *Leuconostocaceae*", Int. J. Syst. Evol. 2020. 70. 2782-2858.

Salami et al., "Probiotic treatment reduces blood glucose levels and increases systemic absorption of gliclazide in diabetic rats", Eur. J. Drug Metabolism and Pharmacokinetics, 2008, vol. 33, No. 2, pp. 101-106.

Kharkevich, 10th ed . M.: GEOTAR-Media , p. 908 (2010).

Zhulenko et al., Pharmacology, Textbooks and Teaching Aids for Students, Higher Educational Institutions, 4 pgs. (2008).

* cited by examiner

USE OF LACTIC ACID BACTERIA TO TREAT OR PREVENT GESTATIONAL DIABETES MELLITUS

REFERENCE TO RELATED APPLICATIONS

This application is the U.S. National Phase of International Application PCT/IB2017/053262, filed Jun. 2, 2017, and claims priority to NZ Application No. 727914, filed Dec. 22, 2016, each of which is incorporated by reference herein. Any and all applications for which a foreign or domestic priority claim is identified in the Application Data Sheet as filed with the present application are hereby incorporated by reference under 37 C.F.R. § 1.57.

TECHNICAL FIELD

This invention relates to the use of probiotic bacteria and in particular the use of a strain of lactic acid bacteria to treat or prevent gestational diabetes mellitus (GDM). Methods for using the bacteria and compositions comprising the bacteria are also provided.

BACKGROUND

Lifestyle factors such as changes in patterns of food consumption with economic development have led to the well-recognized and increasing problems of obesity and associated diseases, including gestational diabetes mellitus (GDM) both in New Zealand (NZ)[1] and other developed countries[2].

Pre-pregnancy overweight and obesity have been shown to account for 46% of GDM[3] with excess weight gain during pregnancy, previous GDM or a family history of diabetes, polycystic ovary syndrome (PCOS), older age and higher parity also identified as risk factors[4]. GDM itself increases the risk of preeclampsia, miscarriage, preterm birth, macrosomia, induction of labour and caesarean section[2, 3]. GDM also increases the risk of later maternal and child obesity and subsequent type 2 diabetes mellitus[5].

There is currently no international consensus on diagnostic criteria for GDM. One diagnostic criteria by the International Association of Diabetes and Pregnancy Study Group (IADPSG) is an oral glucose tolerance test threshold of ≥5.1 mmol/L (fasting plasma glucose), or post 75 g glucose level at 1 hour of ≥10 mmol/L or at 2 hours ≥8.5 mmol/L. The New Zealand Ministry of Health guideline definitions for GDM specify a higher baseline and 2 hour glucose test threshold (fasting plasma glucose ≥5.5 mmol/L or 2 hours post 75 g glucose level ≥9 mmol/L)[1].

Current treatment or prevention of GDM is generally based on the maintenance of a healthy lifestyle in the subject. Prevention of GDM may include maintaining a healthy weight and blood sugar during pregnancy through diet restrictions and regular exercise. Treatment may also include daily blood glucose testing and insulin injections. Dietary counseling is another method currently used to prevent GDM.

There remains a need for methods and compositions useful to treat or prevent obesity and related diseases, in particular GDM, and particularly methods and compositions utilizing or comprising other lactobacilli. There is also a need for methods and compositions for treating or preventing GDM which does not rely changes in dietary modification and counseling. Methods and compositions for the prevention or amelioration of GDM-associated risks or sequelae of GDM are also desirable.

It is an object of this invention to go some way towards achieving one or more of these desiderata or at least to offer the public a useful choice.

SUMMARY OF THE INVENTION

In a first aspect the invention provides a method of treating or preventing GDM in a subject, the method comprising administration of *Lactobacillus rhamnosus* HN001, AGAL deposit number NM97/09514 dated 18 Aug. 1997 to a subject in need thereof.

In one embodiment, the *L. rhamnosus* HN001 is administered in the form of a composition with a physiologically acceptable diluent, adjuvant, carrier or excipient.

In one embodiment, HN001 is the only probiotic bacteria administered.

In one embodiment, HN001 is administered with one or more prebiotics.

In one embodiment, said physiologically acceptable diluent, adjuvant, carrier or excipient is a food. In one embodiment, the food is cultured milk, yoghurt, cheese, milk drink or milk powder.

Alternatively the composition is a pharmaceutical composition and said excipient or diluent is pharmaceutically acceptable diluent, adjuvant, carrier or excipient.

In another aspect the invention provides a method of treating or preventing one or more GDM-associated risks or one or more sequelae of GDM in a subject, the method comprising administration of *Lactobacillus rhamnosus* HN001, AGAL deposit number NM97/09514 dated 18 Aug. 1997 to a subject in need thereof.

In embodiments where the subject is a foetal subject, the method of treating or preventing one or more GDM-associated risks or one or more sequelae of GDM comprises administering the *L. rhamnosus* HN001 or a composition comprising *L. rhamnosus* HN001 to the foetal subject's mother. It will be appreciated that in such embodiments, the administration to the subject may be considered indirect administration. In one embodiment, the composition is a maternal formula or a maternal supplement.

In certain embodiments where the subject is a neonatal, an infant, or a child subject, the method of treating or preventing one or more GDM-associated risks or one or more sequelae of GDM comprises administering a composition comprising *L. rhamnosus* HN001 to the subject. It will be appreciated that in such embodiments, the administration to the subject may be considered direct administration.

In other embodiments, such as where the subject is a breastfeeding neonatal, infant, or child subject, the method of treating or preventing one or more GDM-associated risks or one or more sequelae of GDM comprises administering the *L. rhamnosus* HN001 or a composition comprising *L. rhamnosus* HN001 to the subject's mother. It will be appreciated that in such embodiments, the administration to the subject may be considered indirect administration.

The composition may be a formula, for example a maternal formula follow-on formula, growing-up formula or dietetic product, including hypoallergenic embodiments of such compositions.

In preferred embodiments where the subject is an adult subject, the method comprises administering a composition comprising *L. rhamnosus* HN001 to the subject. Preferably, the composition is a supplement, formula, dietetic product or food.

In certain embodiments, the *L. rhamnosus* HN001 is in a reproductively viable form, preferably in a reproductively viable form and amount. In other embodiments, the *L. rhamnosus* HN001 is killed, lysed, fractionated or attenuated.

The invention further provides *L. rhamnosus* HN001, or a derivative thereof, for treating or preventing GDM, or for treating or preventing one or more GDM-associated risks or one or more sequelae of GDM, and *L. rhamnosus* HN001, or a derivative thereof, in the manufacture of a composition for treating or preventing GDM or for treating or preventing one or more GDM-associated risks or one or more sequelae of GDM. The composition may be a composition such as those as described below including, for example, a food or medicament.

It will be appreciated that the invention also contemplates the use of *L. rhamnosus* HN001 in the manufacture of a composition of the invention, for example a composition for treating or preventing GDM in a subject.

In one embodiment the composition is suitable for oral administration. In other embodiments, the composition is suitable for parenteral administration. In embodiments relating to preventing one or more GDM-associated risks or one or more sequelae of GDM in a foetal subject, the composition is suitable for oral administration to a pregnant mother during gestation.

In various embodiments, the method is a method of treating or preventing GDM in a subject having an increased risk of GDM. In one example, the method is a method of treating or preventing GDM in a subject who has previously suffered GDM. In one example, the method is a method of treating or preventing GDM in an subject over the age of 35 years, for example, a subject over the age of 35 years at conception. In another example, the method is a method of treating or preventing GDM in a subject who has previously been pregnant.

In various embodiments, the subject has a BMI of less than 30 kg/m2.

In one embodiment, the method is a method of preventing recurrence of GDM in a subject who has previously suffered from GDM, the method comprising administering an effective amount of HN001 or a derivative thereof to a subject in need thereof.

In one embodiment, the method comprises beginning administration of HN001 after the first trimester of pregnancy. In one embodiment, administration of HN001 begins between 14-16 weeks gestation.

In one aspect, the invention relates to a method of lowering fasting mean blood glucose levels in a subject, the method comprising administering an effective amount of HN001 or a derivative thereof to a subject in need thereof.

In one embodiment, the fasting mean blood glucose level is below about 4.35 mmol/l.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

DETAILED DESCRIPTION OF THE INVENTION

Figure 1:
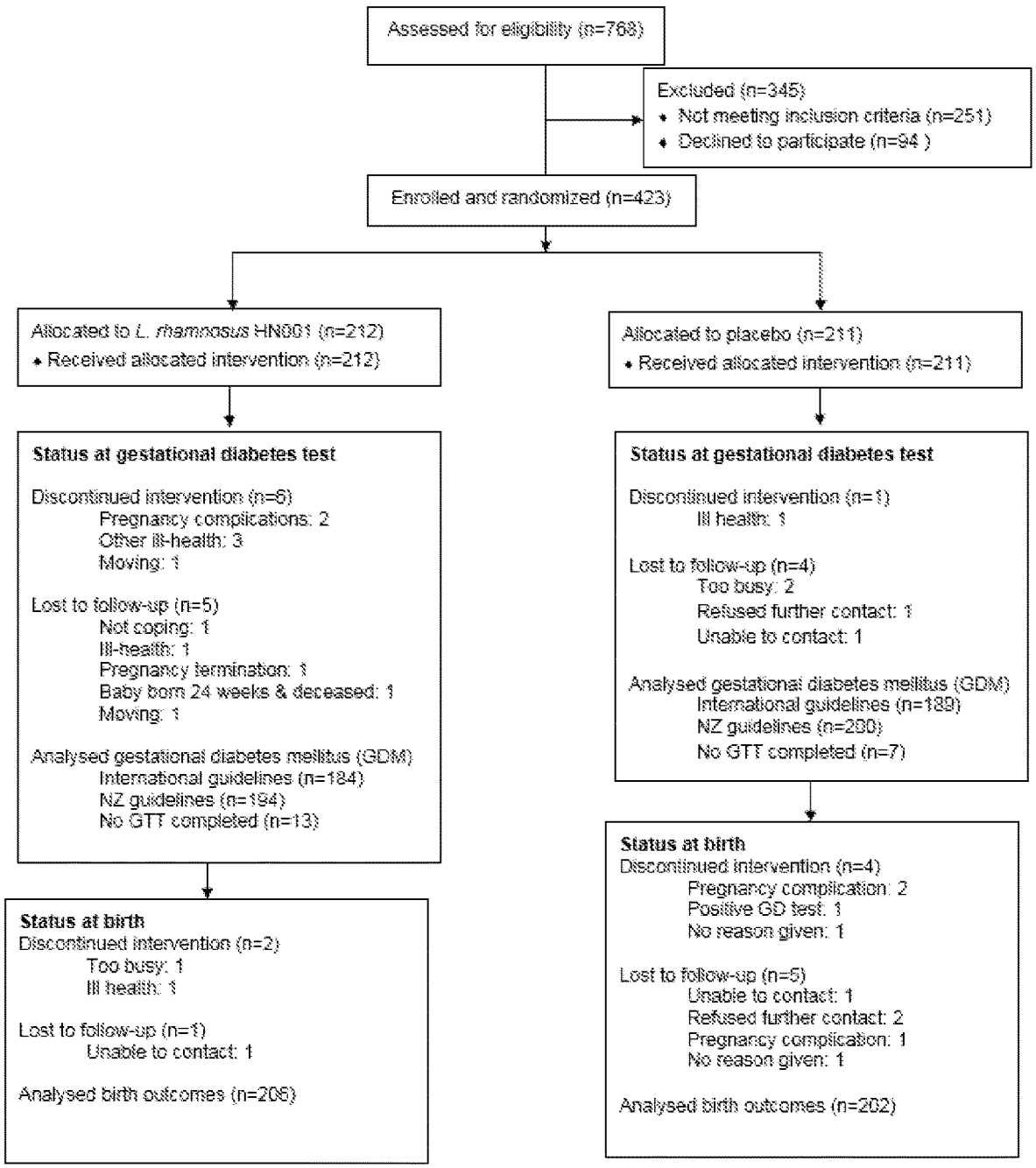
FIG. 1 is a diagram of the status of study participants through the trial

The present invention recognises for the first time the beneficial effects of administration of the lactic acid bacteria *L. rhamnosus* HN001 on the incidence and severity of GDM.

Accordingly, in a first aspect the invention provides a method of treating or preventing GDM in a subject, the method comprising administration of *Lactobacillus rhamnosus* HN001, AGAL deposit number NM97/09514 dated 18 Aug. 1997 or a derivative thereof to a subject in need thereof.

In a further aspect, the invention also provides a method of treating or preventing GDM-associated risks or sequelae of GDM in a subject, the method comprising administration of *Lactobacillus rhamnosus* HN001 or a derivative thereof to a subject in need thereof. GDM-associated risks in a pregnant subject are, for example but not limited to high blood pressure, urinary tract infections, caesarean birth, and increased risk of type-2 diabetes. GDM-associated risks or sequelae of GDM in a foetal, neonatal, infant, child or adult subject (in particular, subjects whose birth mother suffered from GDM during their period in utero) are, for example but not limited to preterm birth, shoulder dystocia, macrosomia, congenital defects, and neonatal complications such as hypoglycaemia, jaundice and respiratory distress, type 2 diabetes, cardiovascular disease, obesity and metabolic issues.

While various routes and methods of administration are contemplated, oral administration of *L. rhamnosus* HN001, such as in a composition suitable for oral administration, is currently preferred. It will of course be appreciated that other routes and methods of administration may be utilised or preferred in certain circumstances. For example, a parenteral route may be utilised with a composition comprising killed or attenuated *L. rhamnosus* HN001 or a derivative thereof.

The term "oral administration" includes oral, buccal, enteral and intra-gastric administration.

The term "parenteral administration" includes but is not limited to topical (including administration to any dermal, epidermal or mucosal surface), subcutaneous, intravenous, intraperitoneal, and intramuscular administration.

A "subject" is an animal, preferably a mammal, more preferably a mammalian companion animal or human. Preferred companion animals include cats, dogs and horses. In one embodiment the human is an adult, a child, an infant, a neonate, or a foetus. In various embodiments, the human child, infant or neonate is a breastfeeding child, infant or neonate.

The term "treat" and its derivatives should be interpreted in their broadest possible context. The term should not be taken to imply that a subject is treated until total recovery. Accordingly, "treat" broadly includes amelioration and/or prevention of the onset of the symptoms or severity of a particular condition.

It will be appreciated that treatment includes prophylactic treatment, such as for example, the prophylactic treatment of a subject, such as a subject having an expected or established increased risk of GDM and/or a subject attempting to become or recently pregnant, or the prophylactic treatment of one or more GDM-associated risks or one or more sequelae of GDM in a foetal subject by indirect administration of a composition of the invention by administering the composition to the foetal subject's mother.

In another example, the prophylactic treatment of one or more GDM-associated risks or one or more sequelae of GDM is of a neonatal, infant or child subject by indirect administration of a composition of the invention by administering the composition to the subject's breastfeeding mother.

It will be further appreciated that treatment includes therapeutic treatment, such as for example, treatment of GDM or one or more symptoms of or risks associated with GDM, including for example the treatment of an neonatal, infant or child subject by indirect administration of a composition of the invention by administering the composition to the subject's mother.

Accordingly, the invention provides for a method of treating or preventing GDM in a pregnant subject, the method comprising administration of *L. rhamnosus* HN001 or a composition comprising *L. rhamnosus* HN001 to the pregnant subject.

In certain embodiments, the pregnant subject is older, for example 35 years or older.

In certain embodiments, the pregnant subject has a history of GDM.

In certain embodiments, the *L. rhamnosus* HN001 or a composition comprising *L. rhamnosus* HN001 is administered from 14 to 16 weeks gestation until delivery.

In certain embodiments, the *L. rhamnosus* HN001 or a composition comprising *L. rhamnosus* HN001 is administered from 14 to 16 weeks gestation to 6 months postpartum.

Accordingly, the invention provides a method of preventing one or more GDM-associated risks or one or more sequelae of GDM in a foetal subject, the method comprising administration of *L. rhamnosus* HN001 or a composition comprising *L. rhamnosus* HN001 to the subject's mother.

Also provided is a method of treating or preventing one or more GDM-associated risks or one or more sequelae of GDM in a neonatal, infant, or child subject, the method comprises administering *L. rhamnosus* HN001 or a composition comprising *L. rhamnosus* HN001 to the subject's mother.

A method of treating one or more GDM-associated risks or one or more sequelae of GDM in an infant or child subject comprising administering a composition consisting of or consisting essentially of *L. rhamnosus* HN001 is also contemplated.

In certain embodiments, the infant or child is one or more years of age.

In certain embodiments, the infant or child is a food-sensitised infant or child.

In certain embodiments, the infant or child is considered to be at risk of one or more GDM-associated risks or one or more sequelae of GDM due to the prior incidence of GDM in the infant or child's mother.

1 *Lactobacillus rhamnosus* HN001

As described in the applicant's PCT International application PCT/NZ98/00122 (published as WO 99/10476 and incorporated herein in its entirety), a freeze-dried culture of *Lactobacillus rhamnosus* HN001 was deposited at the Australian Government Analytical Laboratories (AGAL), The New South Wales Regional Laboratory, 1 Suakin Street, Pymble, NSW 2073, Australia, on 18 Aug. 1997 and was accorded deposit number NM97/09514. This Budapest Treaty-recognised depository is now no longer referred to as AGAL, but rather is referred to as the National Measurement Institute of Australia (NMIA). The genome sequence of *L. rhamnosus* HN001 is available at Genebank under accession number: NZ_ABWJ00000000.

1.1 Morphological Properties

The morphological properties of *L. rhamnosus* HN001 are described below.

Short to medium rods with square ends in chains, generally 0.7×1.1×2.0-4.0 μm, when grown in MRS broth.

Gram positive, non-mobile, non-spore forming, catalase negative facultative anaerobic rods with optimum growth temperature of 37±1° C. and optimum pH of 6.0-6.5. These are facultatively heterofermentative bacteria and no gas is produced from glucose.

1.2 Fermentative Properties

An API 50 CH sugar fermentation kit was used to determine the carbohydrate fermentation pattern of *L. rhamnosus* HN001, yielding a score of 5757177 (based on scores of 22 prominent sugars—see PCT/NZ98/00122).

1.3 Further Characterisation

*L. rhamnosus* strain HN001 may be further characterised by the functional attributes disclosed in PCT/NZ98/00122, including its ability to adhere to human intestinal epithelial cells, and by the improvements in phagocyte function, in antibody responses, in natural killer cell activity, and in lymphocyte proliferation elicited by dietary intake or in in vitro model systems. It will be appreciated that there are a wide variety of methods known and available to the skilled artisan that can be used to confirm the identity of *L. rhamnosus* HN001, wherein exemplary methods include DNA fingerprinting, genomic analysis, sequencing, and related genomic and proteomic techniques.

As described herein, certain embodiments of the present invention utilise live *L. rhamnosus* HN001. In other embodiments, a *L. rhamnosus* HN001 derivative is utilised.

As used herein, the term "derivative" and grammatical equivalents thereof when used with reference to bacteria (including use with reference to a specific strain of bacteria such as *L. rhamnosus* HN001) contemplates mutants and homologues of or derived from the bacteria, killed or attenuated bacteria such as but not limited to heat-killed, lysed, fractionated, pressure-killed, irradiated, and UV- or light-treated bacteria, and material derived from the bacteria including but not limited to bacterial cell wall compositions, bacterial cell lysates, lyophilised bacteria, probiotic factors from the bacteria, and the like, wherein the derivative retains probiotic activity. Methods to produce such derivatives, such as but not limited to one or more mutants of *L. rhamnosus* HN001 or one or more probiotic factors, and particularly derivatives suitable for administration to a subject (for example, in a composition) are well-known in the art.

It will be appreciated that methods suitable for identifying *L. rhamnosus* HN001, such as those described above, are similarly suitable for identifying derivatives of *L. rhamnosus* HN001, including for example mutants or homologues of *L. rhamnosus* HN001, or for example probiotic factors from *L. rhamnosus* HN001.

The term "probiotic factor" refers to a bacterial molecule responsible for mediating probiotic activity, including but not limited to bacterial DNA motifs, surface proteins, small organic acids, polysaccharides, or cell wall components such as lipoteichoic acids and peptidoglycan, or a mixture of any two or more thereof. While, as noted above, these molecules have not been clearly identified, and without wishing to be bound by any theory, such molecules will be present if a probiotic organism is present.

The term "probiotic activity" refers to the ability of certain microorganisms to stimulate the immune system. Measuring the type and level of activity of a probiotic microorganism is known to those skilled in the art; see, for example, Mercenier et al. (2004), Leyer et al. (2004), or Cummings et al. (2004). For example, probiotic activity may be assessed by a PBMC cytokine secretion assay.

Reference to retaining probiotic activity is intended to mean that a derivative of a probiotic microorganism, such as a mutant or homologue of a probiotic microorganism or an attenuated or killed probiotic microorganism still has useful probiotic activity, or that a composition comprising a probiotic microorganism or a derivative thereof is capable of supporting the maintenance of useful probiotic activity. While the bacterial molecules responsible for mediating probiotic activity have not been clearly identified, molecules that have been proposed as possible candidates include bacterial DNA motifs, surface proteins, small organic acids, polysaccharides, and cell wall components such as lipoteichoic acids and peptidoglycan. It has been postulated that these interact with components of the host immune system to give an immuno-modulatory effect. Preferably, the retained activity is at least about 35, 40, 45, 50, 55, 60, 65, 70, 75, 80, 85, 90, 95, 99 or 100% of the activity of an untreated (i.e., live or non-attenuated) control, and useful ranges may be selected between any of these values (for example, from about 35 to about 100%, from about 50 to about 100%, from about 60 to about 100%, from about 70 to about 100%, from about 80 to about 100%, and from about 90 to about 100%).

Using conventional solid substrate and liquid fermentation technologies well known in the art, *L. rhamnosus* HN001 can be grown in sufficient amounts to allow use as contemplated herein. For example, *L. rhamnosus* HN001 can be produced in bulk for formulation using nutrient film or submerged culture growing techniques, for example under conditions as described in WO99/10476. Briefly, growth is effected under aerobic conditions at any temperature satisfactory for growth of the organism. For example, for *L. rhamnosus* HN001 a temperature range of from 30 to 40° C., preferably 37° C., is preferred. The pH of the growth medium is slightly acidic, preferably about 6.0 to 6.5. Incubation time is sufficient for the isolate to reach a stationary growth phase.

*L. rhamnosus* HN001 cells may be harvested by methods well known in the art, for example, by conventional filtering or sedimentary methodologies (eg. centrifugation) or harvested dry using a cyclone system. *L. rhamnosus* HN001 cells can be used immediately or stored, preferably freeze-dried or chilled at −20° to 6° C., preferably −4° C., for as long as required using standard techniques.

2 Compositions

A composition useful herein may be formulated as a food, drink, food additive, drink additive, dietary supplement, nutritional product, medical food, enteral or parenteral feeding product, meal replacement, cosmeceutical, nutraceutical, or pharmaceutical. Appropriate formulations may be prepared by an art skilled worker with regard to that skill and the teaching of this specification.

In one embodiment, compositions useful herein include any edible consumer product which is able to carry bacteria or a bacterial derivative. Examples of suitable edible consumer products include powders, liquids, confectionary products including chocolate, gels, ice creams, reconstituted fruit products, snack bars, food bars, muesli bars, spreads, sauces, dips, dairy products including yoghurts and cheeses, drinks including dairy and non-dairy based drinks (such as milk drinks and yogurt drinks), milk powders, sports supplements including dairy and non-dairy based sports supplements, food additives such as protein sprinkles, dietary supplement products including daily supplement tablets, weaning foods and yoghurts, and formulas such as maternal formula, in powder or liquid form, including hypoallergenic embodiments of such compositions. Within this embodiment, a preferred composition useful herein may be a maternal formula, in powder or liquid form. Suitable nutraceutical compositions useful herein may be provided in similar forms.

Examples of formulas such as maternal formula, in powder or liquid form, include the following. It should be understood that the following formulations are indicative only and variations may be made according to known principles for formulating such products. For example, non-dairy sources of protein may be supplemented for the dairy proteins listed. Equally, hypoallergenic embodiments of these products may be provided where the protein source is fully or partially hydrolysed. Such hydrolysates are known in the art. One example of a maternal formula, useful herein comprises (w/w)

30-60% lactose
15-35% vegetable oils
0-40% skim milk powder
0-40% whey protein, such as a WPC or WPI, preferably an 80% WPC (WPC80)
0.001-50% of *L. rhamnosus* HN001.

Another example of a maternal formula, useful herein comprises (w/w)

40-60% lactose
20-30% vegetable oils
10-15% skim milk powder
6-8% whey protein, preferably WPC80
0.001-10% of *L. rhamnosus* HN001.

Another example of a maternal formula, herein comprises (w/w)

40-60% lactose
20-30% vegetable oils
10-15% skim milk powder
6-8% whey protein, preferably WPC80
0.001-5% of *L. rhamnosus* HN001.

Another example of a maternal formula, useful herein comprises (w/w)

40-60% lactose
20-30% vegetable oils
10-15% skim milk powder
6-8% whey protein, preferably WPC80
0.001-2% of *L. rhamnosus* HN001.

Any of these formulas may also comprise 0.1 to 4% w/w, preferably 2 to 4% w/w of one or more of a vitamin premix, a mineral premix, lecithin, one or more antioxidants, one or more stabilisers, or one or more nucleotides, or a combination of any two or more thereof. In some embodiments, these infant formulas may be formulated to provide between 2700 and 3000 kJ/L.

Examples of edible consumer products of the invention, such as dairy based drinks (such as milk drinks and yogurt drinks) will typically comprise and may consist of a protein source (such as a dairy protein source), a lipid source, a carbohydrate source, in addition to the *L. rhamnosus* HN001 or derivative thereof. Flavourants, colourants, and other additives, carriers or excipients as are well known to those skilled in the art may also be included.

A further example of an edible consumer product amenable to use in the present invention is the Unistraw™ delivery system (Unistraw International Limited, Australia) as described in PCT international application PCT/AU2007/000265 (published as WO 2007/098564) and PCT international application PCT/AU2007/001698 (published as WO 2008/055296), each incorporated herein in its entirety. It will be appreciated by those skilled in the art that *L. rhamnosus* HN001 and derivatives thereof, optionally together with one or more additional probiotic factor or probiotic agent, may be coated onto a substrate (for example, a water soluble bead) for use in such delivery systems.

In alternative embodiments, the compositions useful herein may be formulated to allow for administration to a subject by any chosen route, including but not limited to oral or parenteral (including topical, subcutaneous, intramuscular and intravenous) administration.

For example, a nutraceutical composition for use according to the invention can be a dietary supplement (e.g., a capsule, a mini-bag, or a tablet) or a food product (e.g., milk, juice, a soft drink, a herbal tea-bag, or confectionary). The composition can also include other nutrients, such as a protein, a carbohydrate, vitamins, minerals, or amino acids. The composition can be in a form suitable for oral use, such as a tablet, a hard or soft capsule, an aqueous or oil suspension, or a syrup; or in a form suitable for parenteral use, such as an aqueous propylene glycol solution, or a buffered aqueous solution. The amount of the active ingredient in the nutraceutical composition depends to a large extent on a subject's specific need. The amount also varies, as recognized by those skilled in the art, dependent on administration route, and possible co-usage of other probiotic factors or probiotic agents.

It will be appreciated that in certain embodiments, the compositions of the invention may be formulated so as to have a desired calorific content, for example so as to deliver a desired amount of energy or a desired percentage of daily recommended energy intake. For example, an edible consumer product may be formulated to provide from about 200 to about 2000 kJ per serve, or from about 500 kJ to about 2000 kJ per serve, or from about 1000 to about 2000 kJ per serve.

Thus, a pharmaceutical composition useful according to the invention may be formulated with an appropriate pharmaceutically acceptable carrier (including excipients, diluents, auxiliaries, and combinations thereof) selected with regard to the intended route of administration and standard pharmaceutical practice. For example, a composition useful according to the invention can be administered orally as a powder, liquid, tablet or capsule, or topically as an ointment, cream or lotion. Suitable formulations may contain additional agents as required, including emulsifying, antioxidant, flavouring or colouring agents, and may be adapted for immediate-, delayed-, modified-, sustained-, pulsed- or controlled-release.

The term "pharmaceutically acceptable carrier" is intended to refer to a carrier including but not limited to an excipient, diluent or auxiliary, pharmaceutically acceptable carrier includes a solvent, a dispersion medium, a coating, an antibacterial and antifungal agent, and an isotonic and absorption delaying agent or combination thereof, that can be administered to a subject as a component of a composition described herein that does not reduce the activity of the composition and is not toxic when administered in doses sufficient to deliver an effective amount of a compound or composition useful herein. The formulations can be administered orally, nasally or parenterally (including topically, intramuscularly, intraperitoneally, subcutaneously and intravenously).

In certain embodiments, a composition of the invention (such as, for example, a nutraceutical or pharmaceutical composition of the invention, may be provided as a capsule. Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tabletting agent. Pharmaceutical compositions can also be administered via the parenteral route. Examples of parenteral dosage forms include aqueous solutions, isotonic saline or 5% glucose of the active agent, or other well-known pharmaceutically acceptable excipients. Cyclodextrins, or other solubilising agents well-known to those familiar with the art, can be utilized as excipients for delivery of the therapeutic agent.

In certain embodiments, the composition of the invention comprises live *L. rhamnosus* HN001. Methods to produce such compositions are well-known in the art, and one such method is exemplified herein in the examples.

In other embodiments, the composition of the invention comprises one or more *L. rhamnosus* HN001 derivative. Again, methods to produce such compositions are well-known in the art, and may utilise standard microbiological and pharmaceutical practices.

It will be appreciated that a broad range of additives or carriers may be included in such compositions, for example to improve or preserve bacterial viability or to increase therapeutic efficacy of *L. rhamnosus* HN001 or of one or more *L. rhamnosus* HN001 derivatives. For example, additives such as surfactants, wetters, humectants, stickers, dispersal agents, stablisers, penetrants, and so-called stressing additives to improve bacterial cell vigor, growth, replication and survivability (such as potassium chloride, glycerol, sodium chloride and glucose), as well as cryoprotectants such as maltodextrin, may be included. Additives may also include compositions which assist in maintaining microorganism viability in long term storage, for example unrefined corn oil, or "invert" emulsions containing a mixture of oils and waxes on the outside and water, sodium alginate and bacteria on the inside.

In certain embodiments, the *L. rhamnosus* HN001 is in a reproductively viable form and amount.

The composition may comprise a carbohydrate source, such as a disaccharide including, for example, sucrose, fructose, glucose, or dextrose. Preferably the carbohydrate source is one able to be aerobically or anaerobically utilised by *L. rhamnosus* HN001.

In such embodiments, the composition preferably is capable of supporting reproductive viability of the *L. rhamnosus* HN001 for a period greater than about two weeks, preferably greater than about one month, about two months, about three months, about four months, about five months, more preferably greater than about six months, most preferably at least about 2 years to about 3 years or more.

In certain embodiments, the composition for treating or preventing GDM or GDM-associated risks or sequelae of GDM comprises a probiotic comprising *L. rhamnosus* HN001 and a prebiotic, for example fructooligosaccharides, galactooligosaccharides, human milk oligosaccharides and combinations thereof.

In another embodiment, the method of treating and preventing GDM or GDM-associated risks or sequelae of GDM in a subject comprises administering an individual with an effective amount of a composition comprising *L. rhamnosus* HN001 and a prebiotic, for example fructooligosaccharides, galactooligosaccharides, human milk oligosaccharides and combinations thereof. In certain embodiments, an oral composition is formulated to allow the administration of a sufficient amount of *L. rhamnosus* HN001 to establish a population in the gastrointestinal tract of the subject when ingested. The established population may be a transient or permanent population.

In theory one colony forming unit (cfu) should be sufficient to establish a population of *L. rhamnosus* HN001 in a subject, but in actual situations a minimum number of units are required to do so. Therefore, for therapeutic mechanisms that are reliant on a viable, living population of probiotic bacteria, the number of units administered to a subject will affect therapeutic efficacy.

As presented herein in the examples, the Applicants have determined that a dosage rate of $6 \times 10^9$ cfu *L. rhamnosus* HN001 per day is sufficient (but may not be necessary) to establish a population in the gastrointestinal tract of human subjects. Accordingly, in one example, a composition formulated for administration will be sufficient to provide at least about $6 \times 10^9$ cfu *L. rhamnosus* HN001 per day.

Methods to determine the presence of a population of gut flora, such as *L. rhamnosus* HN001, in the gastrointestinal tract of a subject are well known in the art, and examples of such methods are presented herein. In certain embodiments, presence of a population of *L. rhamnosus* HN001 can be determined directly, for example by analysing one or more samples obtained from a subject, and determining the presence or amount of *L. rhamnosus* HN001 in said sample. In other embodiments, presence of a population of *L. rhamnosus* HN001 can be determined indirectly, for example by observing a reduction in GDM symptoms, or a decrease in the number of other gut flora in a sample obtained from a subject. Combinations of such methods are also envisaged.

The efficacy of a composition useful according to the invention can be evaluated both in vitro and in vivo. See, for example, the examples below. Briefly, the composition can be tested for its ability to prevent or treat GDM, or to modulate glucose tolerance. For in vivo studies, the composition can be fed to or injected into an animal model (e.g., a mouse) or administered to human subjects (including pregnant women) and its effects on incidence and severity of GDM or glucose tolerance and associated conditions are then assessed. Based on the results, an appropriate dosage range and administration route can be determined.

Methods of calculating appropriate dose may depend on the nature of the active agent in the composition. For example, when the composition comprises live *L. rhamnosus* HN001, the dose may be calculated with reference to the number of live bacteria present. For example, as described herein the examples the dose may be established by reference to the number of colony forming units (cfu) to be administered per day. In examples where the composition comprises one or more *L. rhamnosus* HN001 derivatives, the dose may be calculated by reference to the amount or concentration of *L. rhamnosus* HN001 derivative present. For example, for a composition comprising *L. rhamnosus* HN001 cell lysate, the dose may be calculated by reference to the concentration of *L. rhamnosus* HN001 cell lysate present in the composition.

By way of general example, the administration of from about $1 \times 10^6$ cfu to about $1 \times 10^{12}$ cfu of *L. rhamnosus* HN001 per kg body weight per day, preferably about $1 \times 10^6$ cfu to about $1 \times 10^{11}$ cfu/kg/day, about $1 \times 10^6$ cfu to about $1 \times 10^{10}$ cfu/kg/day, about $1 \times 10^6$ cfu to about $1 \times 10^9$ cfu/kg/day, about $1 \times 10^6$ cfu to about $1 \times 10^8$ cfu/kg/day, about $1 \times 10^6$ cfu to about $5 \times 10^7$ cfu/kg/day, or about $1 \times 10^6$ cfu to about $1 \times 10^7$ cfu/kg/day, is contemplated. Preferably, the administration of from about $5 \times 10^6$ cfu to about $5 \times 10^8$ cfu per kg body weight of *L. rhamnosus* HN001 per day, preferably about $5 \times 10^6$ cfu to about $4 \times 10^8$ cfu/kg/day, about $5 \times 10^6$ cfu to about $3 \times 10^8$ cfu/kg/day, about $5 \times 10^6$ cfu to about $2 \times 10^8$ cfu/kg/day, about $5 \times 10^6$ cfu to about $1 \times 10^8$ cfu/kg/day, about $5 \times 10^6$ cfu to about $9 \times 10^7$ cfu/kg/day, about $5 \times 10^6$ cfu to about $8 \times 10^7$ cfu/kg/day, about $5 \times 10^6$ cfu to about $7 \times 10^7$ cfu/kg/day, about $5 \times 10^6$ cfu to about $6 \times 10^7$ cfu/kg/day, about $5 \times 10^6$ cfu to about $5 \times 10^7$ cfu/kg/day, about $5 \times 10^6$ cfu to about $4 \times 10^7$ cfu/kg/day, about $5 \times 10^6$ cfu to about $3 \times 10^7$ cfu/kg/day, about $5 \times 10^6$ cfu to about $2 \times 10^7$ cfu/kg/day, or about $5 \times 10^6$ cfu to about $1 \times 10^7$ cfu/kg/day, is contemplated.

In certain embodiments, periodic dose need not vary with body weight or other characteristics of the subject. In such examples, the administration of from about $1 \times 10^6$ cfu to about $1 \times 10^{13}$ cfu of *L. rhamnosus* HN001 per day, preferably about $1 \times 10^6$ cfu to about $1 \times 10^{12}$ cfu/day, about $1 \times 10^6$ cfu to about $1 \times 10^{11}$ cfu/day, about $1 \times 10^6$ cfu to about $1 \times 10^{10}$ cfu/day, about $1 \times 10^6$ cfu to about $1 \times 10^9$ cfu/day, about $1 \times 10^6$ cfu to about $1 \times 10^8$ cfu/day, about $1 \times 10^6$ cfu to about $5 \times 10^7$ cfu/day, or about $1 \times 10^6$ cfu to about $1 \times 10^7$ cfu/day, is contemplated. Preferably, the administration of from about $5 \times 10^7$ cfu to about $5 \times 10^{10}$ cfu per kg body weight of *L. rhamnosus* HN001 per day, preferably about $5 \times 10^7$ cfu to about $4 \times 10^{10}$ cfu/day, about $5 \times 10^7$ cfu to about $3 \times 10^{10}$ cfu/day, about $5 \times 10^7$ cfu to about $2 \times 10^{10}$ cfu/day, about $5 \times 10^7$ cfu to about $1 \times 10^{10}$ cfu/day, about $5 \times 10^7$ cfu to about $9 \times 10^9$ cfu/day, about $5 \times 10^7$ cfu to about $8 \times 10^9$ cfu/day, about $5 \times 10^7$ cfu to about $7 \times 10^9$ cfu/day, about $5 \times 10^7$ cfu to about $6 \times 10^9$ cfu/day, about $5 \times 10^7$ cfu to about $5 \times 10^9$ cfu/day, about $5 \times 10^7$ cfu to about $4 \times 10^9$ cfu/day, about $5 \times 10^7$ cfu to about $3 \times 10^9$ cfu/day, about $5 \times 10^7$ cfu to about $2 \times 10^9$ cfu/day, or about $5 \times 10^7$ cfu to about $1 \times 10^9$ cfu/day, is contemplated.

For example, as presented herein in the examples, an efficacious dose of freeze-dried *L. rhamnosus* HN001 was determined to be $6 \times 10^9$ cfu per day.

It will be appreciated that the composition is preferably formulated so as to allow the administration of an efficacious dose of *L. rhamnosus* HN001 or one or more derivatives thereof. The dose of the composition administered, the period of administration, and the general administration regime may differ between subjects depending on such variables as the severity of symptoms of a subject, the type of disorder to be treated, the mode of administration chosen, and the age, sex and/or general health of a subject. Furthermore, as described above the appropriate dose may depend on the nature of the active agent in the composition and the manner of formulation. For example, when the composition comprises live *L. rhamnosus* HN001, the dose may be calculated with reference to the number of live bacteria present. For example, as described herein the examples the dose may be established by reference to the number of colony forming units (cfu) to be administered per day. In examples where the composition comprises one or more *L. rhamnosus* HN001 derivatives, the dose may be calculated by reference to the amount or concentration of *L. rhamnosus* HN001 derivative to be administered per day. For example, for a composition comprising *L. rhamnosus* HN001 cell lysate, the dose may be calculated by reference to the concentration of *L. rhamnosus* HN001 cell lysate present in the composition.

It will be appreciated that preferred compositions are formulated to provide an efficacious dose in a convenient form and amount. In certain embodiments, such as but not limited to those where periodic dose need not vary with body weight or other characteristics of the subject, the composition may formulated for unit dosage. It should be appreciated that administration may include a single daily dose or administration of a number of discrete divided doses as may be appropriate. For example, as presented herein in the examples, an efficacious dose of *L. rhamnosus* HN001 may be formulated into a capsule for oral administration.

However, by way of general example, the inventors contemplate administration of from about 1 mg to about 1000 mg per kg body weight of a composition useful herein per day, preferably about 50 to about 500 mg per kg per day, alternatively about 150 to about 410 mg/kg/day or about 110 to about 310 mg/kg/day. In one embodiment, the inventors contemplate administration of from about 0.05 mg to about 250 mg per kg body weight of a composition useful herein.

Examples of infant formula, follow-on formula, or growing-up formula are presented herein. Compositions such as these may be formulated so that the concentration of *L. rhamnosus* HN001 present in the composition is such that an efficacious dose can be prepared using a readily measurable amount of the composition. For example, in certain embodiments, such as for example where the composition is an infant formula, the *L. rhamnosus* HN001 is provided at a concentration sufficient to supply an efficacious dose in an amount of formula capable of being easily measured by a parent or caregiver when preparing the formula for administration, such as, for example, with a measured scoop or similar as are commonly provided with infant formulas. Exemplary non-limiting concentrations of *L. rhamnosus* HN001 for use in such compositions include from about $5 \times 10^5$ cfu per gram of formula to about $10^9$ cfu per gram of formula, or from about $10^6$ cfu per gram of formula to about $10^8$ cfu per gram of formula.

In one embodiment a composition useful herein comprises, consists essentially of, or consists of at least about 0.1, 0.2, 0.5, 1, 5, 10, 15, 20, 25, 30, 35, 40, 45, 50, 55, 60, 65, 70, 75, 80, 85, 90, 95, 99, 99.5, 99.8 or 99.9% by weight of *L. rhamnosus* HN001 or a derivative thereof and useful ranges may be selected between any of these foregoing values (for example, from about 0.1 to about 50%, from about 0.2 to about 50%, from about 0.5 to about 50%, from about 1 to about 50%, from about 5 to about 50%, from about 10 to about 50%, from about 15 to about 50%, from about 20 to about 50%, from about 25 to about 50%, from about 30 to about 50%, from about 35 to about 50%, from about 40 to about 50%, from about 45 to about 50%, from about 0.1 to about 60%, from about 0.2 to about 60%, from about 0.5 to about 60%, from about 1 to about 60%, from about 5 to about 60%, from about 10 to about 60%, from about 15 to about 60%, from about 20 to about 60%, from about 25 to about 60%, from about 30 to about 60%, from about 35 to about 60%, from about 40 to about 60%, from about 45 to about 60%, from about 0.1 to about 70%, from about 0.2 to about 70%, from about 0.5 to about 70%, from about 1 to about 70%, from about 5 to about 70%, from about 10 to about 70%, from about 15 to about 70%, from about 20 to about 70%, from about 25 to about 70%, from about 30 to about 70%, from about 35 to about 70%, from about 40 to about 70%, from about 45 to about 70%, from about 0.1 to about 80%, from about 0.2 to about 80%, from about 0.5 to about 80%, from about 1 to about 80%, from about 5 to about 80%, from about 10 to about 80%, from about 15 to about 80%, from about 20 to about 80%, from about 25 to about 80%, from about 30 to about 80%, from about 35 to about 80%, from about 40 to about 80%, from about 45 to about 80%, from about 0.1 to about 90%, from about 0.2 to about 90%, from about 0.5 to about 90%, from about 1 to about 90%, from about 5 to about 90%, from about 10 to about 90%, from about 15 to about 90%, from about 20 to about 90%, from about 25 to about 90%, from about 30 to about 90%, from about 35 to about 90%, from about 40 to about 90%, from about 45 to about 90%, from about 0.1 to about 99%, from about 0.2 to about 99%, from about 0.5 to about 99%, from about 1 to about 99%, from about 5 to about 99%, from about 10 to about 99%, from about 15 to about 99%, from about 20 to about 99%, from about 25 to about 99%, from about 30 to about 99%, from about 35 to about 99%, from about 40 to about 99%, and from about 45 to about 99%).

In one embodiment a composition useful herein comprises, consists essentially of, or consists of at least about 0.001, 0.01, 0.05, 0.1, 0.15, 0.2, 0.3, 0.4, 0.5, 1, 2, 3, 4, 5, 6, 7, 8, 9, 10, 11, 12, 13, 14, 15, 16, 17, 18 or 19 grams of *L. rhamnosus* HN001 or a derivative thereof and useful ranges may be selected between any of these foregoing values (for example, from about 0.01 to about 1 grams, about 0.01 to about 10 grams, about 0.01 to about 19 grams, from about 0.1 to about 1 grams, about 0.1 to about 10 grams, about 0.1 to about 19 grams, from about 1 to about 5 grams, about 1 to about 10 grams, about 1 to about 19 grams, about 5 to about 10 grams, and about 5 to about 19 grams).

In one embodiment a composition useful herein comprising *L. rhamnosus* HN001 or a derivative thereof additionally comprises about 0.1, 0.5, 1, 5, 10, 15, 20, 25, 30, 35, 40, 45, 50, 55, 60, 65, 70, 75, 80, 85, 90, 95, 97, 99, or 99.9% by weight of fresh whole milk or a milk derivative and useful ranges may be selected between any of these foregoing values (for example, from about 0.1 to about 50%, from about 0.2 to about 50%, from about 0.5 to about 50%, from about 1 to about 50%, from about 5 to about 50%, from about 10 to about 50%, from about 15 to about 50%, from about 20 to about 50%, from about 25 to about 50%, from about 30 to about 50%, from about 35 to about 50%, from about 40 to about 50%, and from about 45 to about 50%). The milk derivative is preferably selected from recombined, powdered or fresh skim milk, recombined or reconstituted whole or skim milk powder, skim milk concentrate, skim milk retentate, concentrated milk, ultrafiltered milk retentate, milk protein concentrate (MPC), milk protein isolate (MPI), calcium depleted milk protein concentrate (MPC), low fat milk, low fat milk protein concentrate (MPC), casein, caseinate, milk fat, cream, butter, ghee, anhydrous milk fat (AMF), buttermilk, butter serum, beta serum, hard milk fat fractions, soft milk fat fractions, sphingolipid fractions, milk fat globular membrane fractions, milk fat globular membrane lipid fractions, phospholipid fractions, complex lipid fractions, colostrum, a colostrum fraction, colostrum protein concentrate (CPC), colostrum whey, an immunoglobulin fraction from colostrum, whey (including sweet whey, lactic acid whey, mineral acid whey, or reconstituted whey powder), whey protein isolate (WPI), whey protein concentrate (WPC), a composition derived from any milk or colostrum processing stream, a composition derived from the retentate or permeate obtained by ultrafiltration or microfiltration of any milk or colostrum processing stream, a composition derived from the breakthrough or adsorbed fraction obtained by chromatographic (including but not limited to ion and gel permeation chromatography) separation of any milk or colostrum processing stream, extracts of any of these milk derivatives including extracts prepared by multistage fractionation, differential crystallisation, solvent fractionation, supercritical fractionation, near critical fractionation, distillation, centrifugal fractionation, or fractionation with a modifier (e.g. soaps or emulsifiers), hydrolysates of any of these derivatives, fractions of the hydrolysates, and any combination of any two or more of these derivatives, including combinations of hydrolysed and/or non-hydrolysed fractions. It should be understood that the source of these derivatives may be milk or colostrum or a combination thereof.

It will be apparent that the concentration of L. rhamnosus HN001 or one or more derivatives thereof in a composition formulated for administration may be less than that in a composition formulated for, for example, distribution or storage, and that the concentration of a composition formulated for storage and subsequent formulation into a composition suitable for administration must be adequate to allow said composition for administration to also be sufficiently concentrated so as to be able to be administered at a therapeutically efficacious dose.

The compositions useful herein may be used alone or in combination with one or more other therapeutic agents. The therapeutic agent may be a food, drink, food additive, drink additive, food component, drink component, dietary supplement, nutritional product, medical food, nutraceutical, medicament or pharmaceutical. The therapeutic agent may be a probiotic agent or a probiotic factor, and is preferably effective to treat, prevent or attenuate GDM or one or more of the symptoms of GDM, or one or more GDM-associated risks or one or more sequelae of GDM.

When used in combination with another therapeutic agent, the administration of a composition useful herein and the other therapeutic agent may be simultaneous or sequential. Simultaneous administration includes the administration of a single dosage form that comprises all components or the administration of separate dosage forms at substantially the same time. Sequential administration includes administration according to different schedules, preferably so that there is an overlap in the periods during which the composition useful herein and other therapeutic agent are provided.

Suitable agents with which the compositions useful herein can be separately, simultaneously or sequentially administered include one or more probiotic agents, one or more prebiotic agents, one or more phospholipids, one or more gangliosides, other suitable agents known in the art, and combinations thereof. Useful prebiotics include galactooligosaccharides (GOS), short chain GOS, long chain GOS, fructooligosaccharides (FOS), human milk oligosaccharides (HMO), short chain FOS, long chain FOS, inulin, galactans, fructans, lactulose, and any mixture of any two or more thereof. Some prebiotics are reviewed by Boehm G and Moro G (Structural and Functional Aspects of Prebiotics Used in Infant Nutrition, J. Nutr. (2008) 138(9):1818S-1828S), incorporated herein by reference. Other useful agents may include dietary fibre such as a fully or partially insoluble or indigestible dietary fibre. Accordingly, in one embodiment L. rhamnosus HN001 or derivative thereof may be administered separately, simultaneously or sequentially with one or more agents selected from one or more probioitics, one or more prebiotics, one or more sources of dietary fibre, one or more galactooligosaccharides, one or more short chain galactooligosaccharides, one or more long chain galactooligosaccharides, one or more fructooligosaccharides, one or more short chain galactooligosaccharides, one or more long chain galactooligosaccharides, one or more human milk oligosaccharides, inulin, one or more galactans, one or more fructans, lactulose, or any mixture of any two or more thereof.

In one embodiment, a composition useful herein includes or is administered simultaneously or sequentially with milk components such as whey protein, whey protein fractions (including acidic or basic whey protein fractions or a combination thereof), glycomacropeptide, lactoferrin, iron-lactoferrin, a functional lactoferrin variant, a functional lactoferrin fragment, a vitamin D or calcium, or combinations thereof. Useful milk component-containing compositions include compositions such as a food, drink, food additive, drink additive, dietary supplement, nutritional product, medical food or nutraceutical. Milk fractions enriched for these components may also be employed. Useful lactoferrins, fragments and compositions are described in international patent applications WO 03/082921 and WO 2007/043900, both incorporated herein by reference in their entirety.

It should be understood that the additional therapeutic agents listed above (both food based and pharmaceutical agents) may also be employed in a method according to the invention where they are administered separately, simultaneously or sequentially with a composition useful herein.

In one embodiment a composition useful herein further comprises a pharmaceutically acceptable carrier. In another embodiment the composition is or is formulated as a food, drink, food additive, drink additive, dietary supplement, nutritional product, medical food, enteral feeding product, parenteral feeding product, meal replacement, cosmeceutical, nutraceutical, medicament, or pharmaceutical. In one embodiment the composition is in the form of a tablet, a caplet, a pill, a hard or soft capsule or a lozenge. In one embodiment the composition is in the form of a cachet, a powder, a dispensable powder, granules, a suspension, an elixir, a liquid, or any other form that can be added to food or drink, including for example water, milk or fruit juice. In one embodiment the composition further comprises one or more constituents (such as antioxidants) which prevent or reduce degradation of the composition during storage or after administration. These compositions may include any edible consumer product which is able to carry bacteria or bacterial derivatives, including heat-killed, pressure-killed, lysed, UV- or light-treated, irradiated, fractionated or otherwise killed or attenuated bacteria. Examples of suitable edible consumer products include aqueous products, baked goods, confectionary products including chocolate, gels, ice creams, reconstituted fruit products, snack bars, food bars, muesli bars, spreads, sauces, dips, dairy products including yoghurts and cheeses, drinks including dairy and non-dairy based drinks, milk, milk powders, sports supplements including dairy and non-dairy based sports supplements, fruit juice, food additives such as protein sprinkles, dietary supplement products including daily supplement tablets, weaning foods and yoghurts, and formulas such as infant formula, follow-on formula, or growing-up formula, in powder or liquid form. Suitable nutraceutical compositions useful herein may be provided in similar forms.

It will be appreciated that different compositions of the invention may be formulated with a view to administration to a particular subject group. For example, the formulation of a composition suitable to be administered to a pregnant mother (for example, for indirect administration to a foetal subject or to a breastfeeding neonatal, infant, or child subject) may differ to that of a composition to be directly administered to the subject. It should also be appreciated that the formulation of a composition to be administered prophylactically may differ to that of a composition formulated for administration once GDM or one or more symptoms of GDM is present.

In one embodiment the composition for prophylactic use may further comprise or the *L. rhamnosus* HN001 may be used in combination with a probiotic agent such as *Lactobacillus rhamnosus* GG, *Lactobacillus acidophilus* (for example, *Lactobacillus acidophilus* (LAVRI-A1), *Lactobacillus reuteri* (for example *Lactobacillus reuteri* ATCC 55730) or *Bifidobacteria lactis* (for example, *Bifidobacteria lactis* strain HN019 or *Bifidobacterium lactis* Bbl2) or a combination of any two or more thereof.

In one embodiment, compositions for prophylactic administration, and particularly prophylactic indirect administration, may further comprise or the *L. rhamnosus* HN001 may be used in combination with a probiotic agent such as *Lactobacillus rhamnosus* GG, *Lactobacillus acidophilus* (for example, *Lactobacillus acidophilus* (LAVRI-A1), *Lactobacillus reuteri* (for example *Lactobacillus reuteri* ATCC 55730) or *Bifidobacteria lactis* (for example, *Bifidobacteria lactis* strain HN019) or a combination of any two or more thereof.

It will be appreciated that the term "prophylactic" and grammatical equivalents as used herein contemplates treatment, use, administration and the like before GDM or the symptoms of GDM are apparent.

In embodiments for use in the treatment of a subject having GDM or one or more symptoms of GDM, the composition may further comprise or the *L. rhamnosus* HN001 may be combination with a probiotic agent such as *Lactobacillus rhamnosus* GG, *Lactobacillus acidophilus* (for example, *Lactobacillus acidophilus* (LAVRI-A1), *Lactobacillus reuteri* (for example *Lactobacillus reuteri* ATCC 55730) or *Bifidobacteria lactis* (for example, *Bifidobacteria lactis* strain HN019) or a combination of any two or more thereof.

As used herein, the term "therapeutic" and grammatical equivalents contemplate treatment, uses or administration where GDM or the symptoms of GDM are present.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

3 Gestational Diabetes Mellitus

Accompanying the worldwide trends in obesity, the rate of gestational diabetes mellitus (GDM) is also increasing in both the developed and the developing world[10]. GDM generally affects between 9% and 26% of all pregnancies depending on country and ethnic group. In certain cases the prevalence of GDM is as high as 36%. Using the IADPSG[11] diagnostic criteria, 18% of pregnant women in the United States develop GDM during pregnancy[10]. There is a strong trend for increasing prevalence over the past 20 years.

GDM is associated with short and long-term adverse outcomes for both women and infants, including maternal gestational hypertension, polyhydramnios, preeclampsia, delivery of large-for-gestation infants, instrumental or caesarean delivery, and maternal death[10, 12].

Adverse infant outcomes include preterm birth, shoulder dystocia, macrosomia, congenital defects, and neonatal complications such as hypoglycaemia, jaundice and respiratory distress[10]. In addition, in the longer term, women with GDM are at increased risk of metabolic syndrome[13], type 2 diabetes, and cardiovascular disease. Offspring of women with GDM have an increased risk of diabetes, obesity and metabolic issues with evidence of altered insulin secretion and lipid profiles regardless of the infant's weight[14].

Lifestyle interventions to prevent GDM relating to diet, weight loss and exercise are often unsuccessful[10, 15]; therefore primary prevention of GDM could provide substantial multigenerational health and economic benefits.

Various aspects of the invention will now be illustrated in non-limiting ways by reference to the following examples.

Example

To determine whether probiotic *Lactobacillus rhamnosus* HN001 (HN001) taken by pregnant mothers from early pregnancy could reduce the prevalence of GDM by 26-28 weeks gestation, a double blind, randomized, placebo-controlled parallel trial was conducted.

Materials and Methods

Pregnant women in Auckland and Wellington, NZ, were recruited to the study via health professionals and study information placed in pregnancy packs. Women were considered eligible if they were less than 16 weeks gestation, English-speaking, intending to breastfeed and if either they or the unborn child's biological father had a history of asthma, hayfever or eczema requiring medication. Women were excluded from the study if aged less than 16 years, planning to move outside the study centres during study duration, had a history of immunological disorders or medication, cardiac valve disease, required in-vitro fertilization, had major fetal abnormalities, were using probiotic drinks or supplements, participating in another randomized controlled trial (RCT), refused notification of their clinical carers, carried adrenaline for cows' milk allergy, had a history of a transplant or HIV, had used continuous antibiotic therapy for at least 3 months, miscarried between screening and enrolment, or were otherwise deemed unsuitable. Eligible women were enrolled into the study at 14-16 weeks gestation, where gestation was based on the earliest first trimester scan and, where this was not available, the date of the last menstrual period.

Study Design

Participating women were randomized to receive capsules containing either HN001 ($6 \times 10^9$ colony forming units (cfu)) or placebo (corn derived maltodextrin, identical in appearance and smell to the probiotic) to be taken daily from enrolment throughout pregnancy and up till six months post birth if still breastfeeding. HN001 powder was manufactured by Fonterra Co-operative Group Ltd using aseptic fermentation, concentration and freeze-drying, as previously described[8]. The placebo powder, corn-derived maltodextrin, was manufactured by Grain Processing Corp. Oregon, USA. Women were instructed to keep the capsules in the refrigerator and to avoid taking them within 10 minutes of consuming hot food or fluid.

Fonterra retained samples of capsules at 4° C. which were tested monthly to ensure viability of the contents over time. The viability of the contents of a selection of unused capsules returned from the field was tested three monthly. Loss in viability was less than 0.1 log, and within the limit of uncertainty of the counting method.

Randomization of capsules was performed by a statistician at Fonterra who had no contact with study investigators or participants. Randomization was stratified by study centre and performed in blocks of 20 according to a computer-generated randomization schedule and an allocation ratio of 1:1. Research staff screened and enrolled participants, providing eligible participants with the next available sequentially-numbered capsule container. All researchers, laboratory staff and participants were blind to study allocation.

Baseline information collected included age, ethnicity, parity, previous polycystic ovary syndrome (PCOS), body mass index (BMI) (weight (kg)/height (m)$^2$), waist circumference, antibiotic use during pregnancy but prior to enrolment and type 2 diabetes mellitus in the participant or a first degree relative. Among women with previous pregnancies greater than 20 weeks, we also collected a history of previous GDM and birth weight of previous babies.

Outcome Measures

The GDM outcome was defined a priori primarily as the diagnosis of GDM according to the IADPSG recommendations[6]: a fasting plasma glucose ≥5.1 mmol/L, or post 75 g glucose load of ≥10 mmol/l at 1 hour or ≥8.5 mmol/l at 2 hours. A secondary analysis was conducted using NZ thresholds of ≥5.5 mmol/l fasting or ≥9 mmol/l at 2 hours to define GDM[1].

The assessment for GDM was conducted at 24-30 weeks gestation following a 12 hour overnight fast, using a glucose tolerance test (GTT) undertaken at a community laboratory. Only women without pre-pregnancy diabetes were invited to undertake a study GTT. Women who received a GTT based diagnosis of GDM prior to the study GTT were included in the study outcome only if there was evidence of earlier negative tests confirming their diabetes was gestational. When repeat GTTs were performed later in pregnancy (for clinical purposes), the test completed at 24-30 weeks gestation determined their study GDM status.

Women with GDM were asked to have a post-partum HbA1$_c$ at least 3 months after birth. A post-partum HbA1$_c$ level ≥6.5% (48 mmol/mol) or a post-partum fasting glucose ≥7 mmol/l and/or 2 hour glucose ≥11.1 mmol/l was used to indicate the presence of co-existing type 2 diabetes. If women met these criteria they were excluded from the GDM analysis.

Other outcomes were collected at 4-7 days post birth, including maternal weight (kg) and waist circumference (cm), gestation (in weeks) and prematurity (<37 weeks). Infant Apgar score at five minutes and birth weight were collected from medical records. Infant length (cm), Ponderal index (PI) (birth weight (kg)/length (m)$^3$), head circumference (cm), type of delivery (vaginal or caesarean) and admission to the Neonatal Intensive Care Unit (NICU) were assessed by the researcher at 4-7 days post birth.

Adherence

More than three months' supply of capsules (n=105) was placed in each bottle. Bottles were replaced at 26-28 weeks gestation and birth, when 2 bottles were given to the mother to cover the period to 6 months post-birth. Returned bottles were counted by staff not involved in study assessments as a measure of adherence.

Power

Assuming a 15% prevalence of GDM, a 63% reduction due to the probiotic as found in a Finnish study[8], and a sample size of 195 in each group the study would have 87% power at the 5% level of significance.

Statistical Analysis

Analysis was undertaken using SAS 9.3 and 9.4 (SAS Institute, Cary, N.C.). All analyses were intention-to-treat. Differences between treatment groups in the prevalence of GDM and dichotomous birth outcomes were estimated using relative rates (RR) and 95% CI. Although not pre-specified, we conducted an analysis of GDM stratified by factors that were significantly associated with GDM (maternal age, BMI, a history of GDM), and by antibiotic use during the study prior to the GTT using a generalized linear model with a log link and binomial distribution. For continuous variables, differences between treatment groups are reported as differences in means (95% CI) compared using t-tests or ratios of geometric means (95% CI) compared using analysis of covariance on logged values, adjusted for logged baseline measures; other differences were compared with Wilcoxon rank-sum tests. Apgar score was compared between groups using ordinal logistic regression. Tests were two-sided and P<0.05 was considered statistically significant.

Missing GTT measurements were estimated with 1,000 multiple imputations using treatment, fasting, one and two hour measurements, ethnicity, age, BMI at enrolment, a family history of diabetes in first degree relatives, previous polycystic ovary syndrome, and the combination of previous GDM and number of previous pregnancies >20 weeks (grouped as no previous pregnancies, one previous pregnancy with GDM, or one previous pregnancy without GDM, two or more previous pregnancies with GDM, or two or more previous pregnancies without GDM). One participant who did not have the GTT because she had been diagnosed with GDM and prescribed insulin from early in pregnancy was assumed to have GDM in all imputations.

This study was conducted according to the guidelines laid down in the Declaration of Helsinki and all procedures involving human subjects were approved by the Multi-Region Health and Disability Ethics Committee. Written informed consent was obtained from all subjects. The trial was registered at the Australia NZ Clinical Trials Registry: ACTRN12612000196842.

Results

Participants (n=423) were randomized to the HN001 (n=212) or placebo group (n=211) between December 2012 and November 2014 at an average rate of 4.2 a week. Gestational diabetes assessments were completed by February 2015 and the final infant was born in May 2015. Loss-to-follow-up rates were similar between study groups but more participants in the HN001 group had discontinued the intervention prior to the GTT (FIG. 1). In contrast, most participants lost to follow-up between the GTT and birth visits were in the placebo group, with small numbers discontinuing the intervention in both study groups. There was one maternal death in the placebo group, due to a subarachnoid haemorrhage.

Among randomized participants, the 24-30 week GTT results included all three time points (fasting, 1 hour and 2 hour values, as required by IADPSG guideline definitions) in 184 (87%) participants in the HN001 group and by 189 (90%) in the placebo group, at mean 27.7 (SD 4.6) and 28.0 (SD=8.6) weeks gestation, respectively. An additional 10 HN001 participants and 11 placebo participants had only the fasting and 2-hour time-point GTT results available, which was sufficient for diagnosis of GDM by standard NZ guidelines. In the HN001 group 194 (92%) and in the placebo group 200 (95%) participated in either GTT assessment, all of whom were able to contribute data to the analysis based on NZ guidelines.

There were no substantial differences between study groups in any maternal characteristic at enrolment, including age, ethnicity, parity, weight, waist, BMI, antibiotic use during pregnancy prior to enrolment, family history of diabetes, household income, and among those with previous births, weight of largest infant and having a history of GDM (Table 1).

TABLE 1

Characteristics of study population at enrolment

| | HN001 (N = 212) | Placebo (N = 211) | p |
|---|---|---|---|
| Previous pregnancy | 67.5% (143/212) | 73.8 (155/210) | 0.15* |
| Diabetes in first degree relative | 17.9% (38/212) | 18.5% (39/211) | 0.88* |
| Previous polycystic ovary syndrome | 8.1% (17/209) | 10.6% (22/208) | 0.39* |
| Age (years), median (interquartile range) | 34 (30-36) (n = 212) | 34 (31-37) (n = 210) | 0.65* |
| Weight (kg), median (interquartile range) | 69 (63-80) (n = 211) | 71 (63-82) (n = 210) | 0.45† |
| Waist circumference (cm), median (interquartile range) | 87 (80-94) (n = 211) | 87 (81-99) (n = 210) | 0.30† |
| BMI, median (interquartile range) | 25 (23-29) (n = 211) | 26 (23-30) (n = 210) | 0.28† |
| Ethnicity | N = 212 | N = 211 | |
| Maori | 10.9% (23) | 16.6% (35) | 0.27* |
| Pacific | 3.8% (8) | 1.9% (4) | |
| Asian | 7.7% (15) | 7.6% (16) | |
| European | 78.3% (166) | 73.5% (155) | |
| Other | 0.0% (0) | 0.5% (1) | |
| Systemic antibiotic use during index pregnancy prior to enrolment | 12.4% (25/201) | 13.9% (28/202) | 0.67* |
| Household income ($NZ) | N = 207 | N = 204 | |
| 0-49k | 8.2% (17) | 7.8% (16) | 0.98* |
| 50-99k | 30.4% (63) | 32.4% (66) | |
| 100-149k | 35.8 (74) | 34.8% (71) | |
| 150 + k | 25.6% (53) | 25.0% (51) | |
| Among women with previous pregnancies ≥20 weeks (n = 248) | | | |
| Previous gestational diabetes | 5.0% (6/121) | 7.1% (9/127) | 0.48* |
| Weight (g) of previous largest baby, median (interquartile range) | 3520 (3260-3900) (n = 119) | 3547 (3232-3856) (n = 124) | 0.62† |
| Macrosomia (previous largest baby ≥4000 g) | 20.2% (24/119) | 14.5% (18/124) | 0.25* |

*Based on chi-squared distribution
†Based ranks

The prevalence of GDM (defined using the IADPSG criteria) in the HN001 group was lower than in the placebo group but this difference was not statistically significant (Table 2). However, using the more specific NZ definition, the prevalence of GDM was significantly lower in the HN001 group. These analyses were repeated with imputed results for missing values but there was little change in the RR estimates. Using the IADPSG guidelines the imputed RR=0.64 (95% CI 0.36, 1.12), and using the NZ guidelines imputed RR=0.39 (95% CI 0.14, 1.07).

Mean blood glucose levels at baseline, and after one and two hours were slightly lower in the HN001 group compared to placebo, but were only significant at baseline (Table 2).

Among those with a history of GDM, HN001 protected against a recurrence of GDM, RR=0.00 (95% CI 0.00-0.66) and for those without prior GDM, RR=0.50, (95% CI 0.20-1.27). Three women (20%) with a history of GDM did not have the GTT completed according to the IADSPG guidelines. In all imputations, these were GDM positive giving an imputed RR=0.38 ((95% CI 0.05-1.00) p=0.043, Barnard's exact test). The HN001 effect on GDM was significantly protective among participants who had not used antibiotics between study enrolment and the GTT test but there was no significant effect of HN001 for those who had used antibiotics during this period.

TABLE 2

Treatment effects on the prevalence (95% CI) of gestational diabetes mellitus defined according to international* and NZ† definitions, and mean (95% CI) blood glucose levels.

|  | HN001 | Placebo | RR (95% CI) | p | Multiple imputation p value |
|---|---|---|---|---|---|
| IADPSG* (n = 373) | 8.2% (15/184) (4.6%, 13.1%) (n = 184) | 13.8% (26/189) (9.2%, 19.5%) (n = 189) | 0.59 (0.32, 1.08) | 0.08 | 0.12 |
| NZ† (n = 394) | 2.1% (4/194) (0.6%, 5.2%) (n = 194) | 6.5% (13/200) (3.5%, 10.9%) (n = 200) | 0.32 (0.11, 0.96) | 0.03 | 0.07 |

|  | (mmol/l) | (mmol/l) | Difference in mean (mmol/l) (95% CI) | | |
|---|---|---|---|---|---|
| Fasting | 4.32 (4.27, 4.37) (n = 195) | 4.40 (4.34, 4.46) (n = 202) | −0.08(−0.15, 0.00) | 0.048 | 0.06 |
| 1 hour | 6.71 (6.46, 6.96) (n = 185) | 6.89 (6.63, 7.15) (n = 189) | −0.18(−0.55, 0.18) | 0.31 | 0.42 |
| 2 hour | 5.65 (5.47, 5.83) (n = 194) | 5.78 (5.57, 5.99) (n = 200) | −0.13(−0.41, 0.15) | 0.36 | 0.39 |

IADPSG, International Association of Diabetes and Pregnancy Study Groups
*Fasting ≥5.1 mmol/l, 1 hour ≥10 mmol/l, 2 hour ≥8.5 mmol/l
†Fasting ≥5.5 mmol/l, 2 hour ≥9 mmol/l Among 44 participants diagnosed with GDM according to either the NZ or IADPSG guidelines, 40 participants had $HbA1_c$ measured between one and fifteen months post birth, with values between 5.0% (31 mmol/mol) and 6.4% (46 mmol/mol). One had a post birth GTT, with values within the normal range. Three participants did not have post-birth a $HbA1_c$, because one declined, one had withdrawn from the study, and one was deceased.

Figure 2:
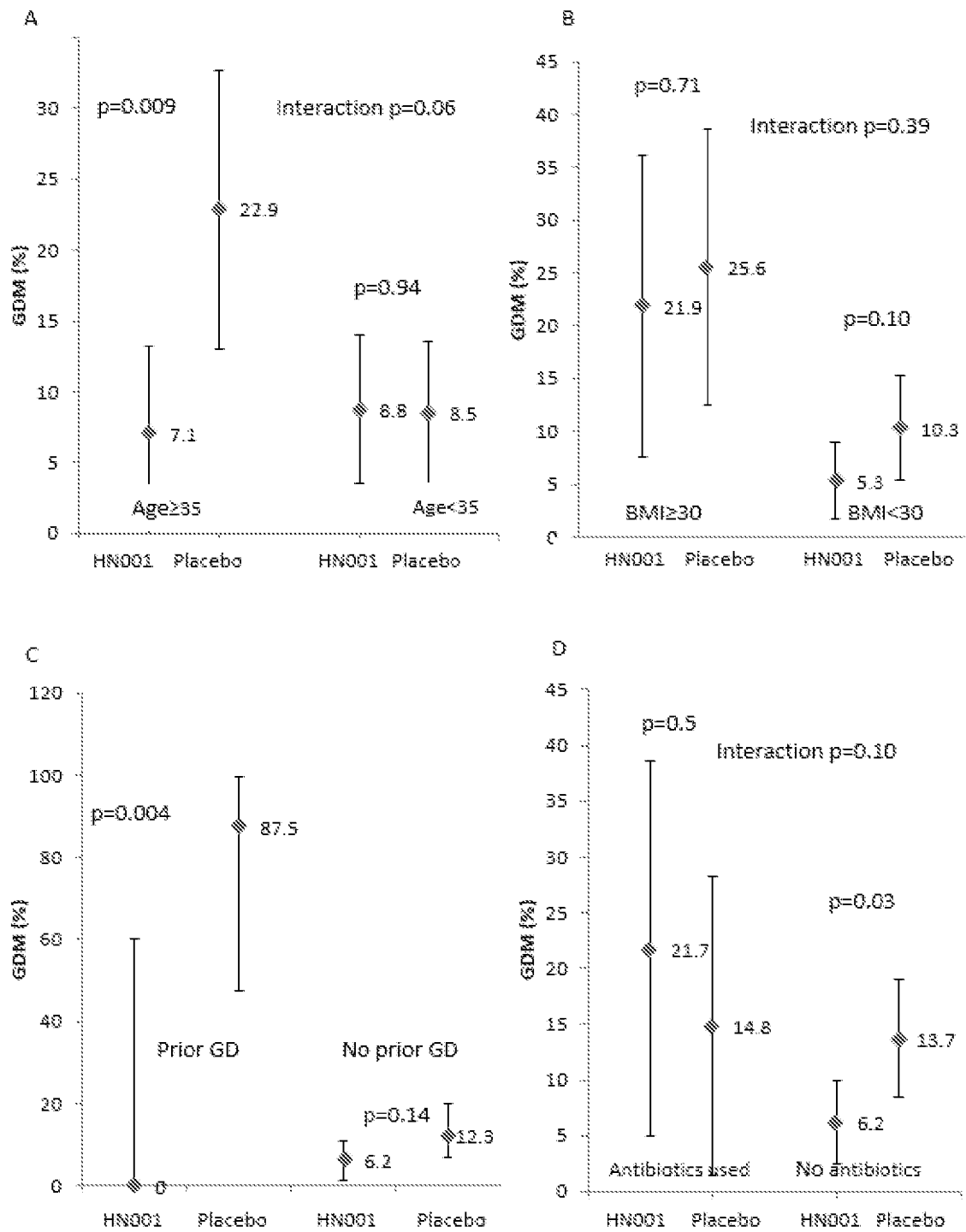
FIG. 2 shows the HN001 associations with GDM stratified by A) Age ≥35 years vs <35 years B) BMI ≥30 kg/m$^2$ vs <30 kg/m$^2$ C) History of GDM D) Systemic antibiotic use since enrolment.

Table 3 shows that maternal age, BMI and having a history of GDM were significantly associated with GDM in this study. These factors were then used to stratify the analysis (FIG. 2), using the IADPSG definition of GDM only. There was a significant treatment by age (as a continuous variable) interaction (p=0.005) and a non-significant interaction with age dichotomised as ≥35 years versus <35 years (p=0.06).

In the older group, HN001 was associated with a three-fold reduction in the prevalence of GDM compared the prevalence among women in the placebo group (RR=0.31 (95% CI 0.12, 0.81), p=0.009). In women aged less than 35 years the prevalence in each study group was similar (RR=1.04 (95% CI 0.45, 2.39)). There were also no significant differences in effect dependent on whether BMI was 30 kg/m² or more (RR=0.86 (95% CI 0.37-1.96)) or less than 30 kg/m² (RR=0.51 (95% CI 0.22-1.17)). An interaction effect could not be tested because GDM did not recur in any of the HN001 participants who had a history of GDM.

Figure 3:
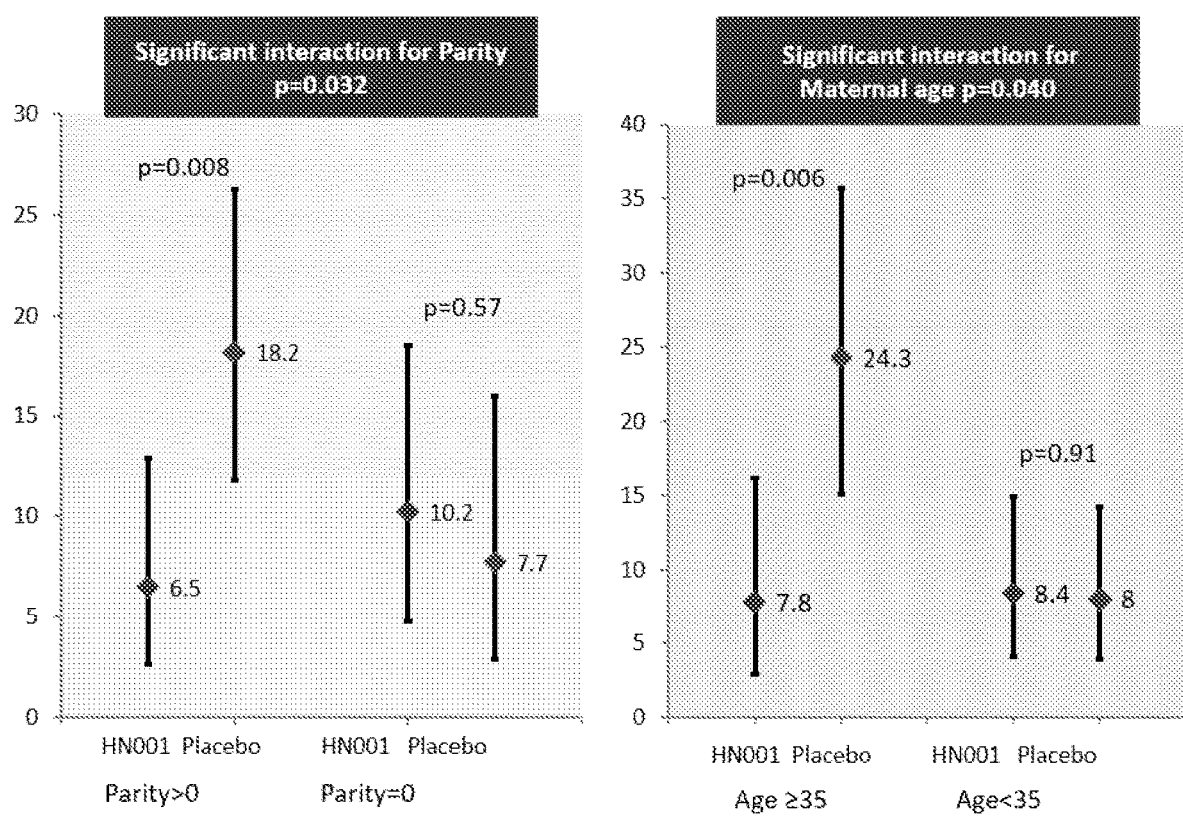
FIG. 3 shows plots of prevalence of GDM by subgroup. The left plot shows the effect of HN001 administration on subjects who had previously been pregnancy vs those who had not (parity, left), and the right plot shows the effect of HN001 administration on subjects over 35 vs those under 35 (maternal age, right).

The prevalence plots depicted in FIG. 3 show the significant interaction for HN001 administration and maternal age (FIG. 3, right plot), where those over 35 years of age benefited more from HN001 than younger mothers, and also the interaction for HN001 administration and previous pregnancy (FIG. 3, parity, left plot), where the effect of HN001 on gestational diabetes was significantly different depending on whether or not woman had a previous pregnancy going beyond 20 weeks. In women who had a previous pregnancy, those on HN001 had about one third the rate of GD compared to those on placebo.

TABLE 3

The association of maternal risk factors with gestational diabetes mellitus, after adjustment for treatment group.

|  | N | RR (95% CI) | p |
|---|---|---|---|
| Maternal age at enrolment* | 372 | 1.11 (1.03, 1.20) | 0.004 |
| Maternal BMI at enrolment† | 371 | 1.11 (1.08, 1.15) | <0.0001 |
| Family history of diabetes | 67/373 | 1.13 (0.55, 2.33) | 0.74 |
| Ethnicity | 373 | | |
| European | 293 | 1.00 | |
| Maori | 46 | 1.49 (0.69, 3.22) | 0.31 |
| Pacific | 7 | 3.05 (0.92, 10.07) | 0.07 |
| Asian | 26 | 1.62 (0.62, 4.22) | 0.32 |
| Polycystic ovary syndrome | 37/367 | 1.19 (0.50, 2.83) | 0.70 |

TABLE 3-continued

The association of maternal risk factors with gestational diabetes mellitus, after adjustment for treatment group.

|  | N | RR (95% CI) | p |
|---|---|---|---|
| Systemic antibiotic use since enrolment | 49/372 | 1.78 (0.91, 3.49) | 0.09 |
| Previous pregnancy (of any duration) | 259/372 | 1.30 (0.66, 2.56) | 0.45 |
| Among women with any previous pregnancy (259/372) | | | |
| Number of miscarriages‡ | 259 | 1.12 (0.78, 1.62) | 0.54 |
| Previous pregnancy >20 weeks | 216/372 | 1.24 (0.68, 2.26) | 0.47 |
| Among women with previous pregnancies ≥20 weeks (216/372) | | | |
| Prior gestational diabetes | 12/216 | 6.59 (3.95, 11.01) | <0.0001 |
| Macrosomia§ in previous child | 35/213 | 0.66 (0.19, 2.35) | 0.53 |

*for each additional year of age
†for each additional BMI unit; two values >45 truncated at 45 to ensure model fit.
‡for each additional miscarriage
§birth weight ≥4000 grams.

Similarly, among those not using antibiotics, fasting mean blood glucose levels were significantly (p=0.001) lower in the HN001 group (4.28, 95% CI 4.23-4.33) compared to the placebo group (4.42, 95% CI 4.35-4.48). Differences in mean glucose levels at one and two hours post glucose load were also lower but were not significant. At one hour, blood glucose levels were 6.63 (95% CI 6.37-6.89) in the HN001 group and 6.88 (95% CI 6.60-7.16) in the placebo group, p=0.20, and at two hours, levels were 5.56 (95% CI 5.38-5.73) in the HN001 and 5.77 (95% CI 5.53-6.01) in the placebo group, p=0.15.

HN001 was not significantly associated with any maternal anthropometric measures (after adjustment for baseline measurements), or infant birth weight, gestation, caesarean delivery or admission to NICU or, at 4-7 days post birth, infant length, PI or head circumference. Infants whose mothers were in the HN001 group had a significantly higher five minute Apgar score than infants in the placebo group (Table 4).

TABLE 4

Treatment effects on birth outcomes

|  | HN001 | Placebo | Geometric mean ratios (95% CI) | p |
|---|---|---|---|---|
| Maternal weight (kg) post birth* (geometric mean, 95% CI) | 76.7 (76.1, 77.2) (n = 197) | 76.8 (76.2, 77.4) (n = 194) | 1.00 (0.99, 1.01) | 0.79 |
| Maternal waist (cm) post birth* (geometric mean, 95% CI) | 97.7 (96.8, 98.7) (n = 195) | 97.3 (96.4, 98.2) (n = 195) | 1.00 (0.99, 1.02) | 0.53 |
| Maternal BMI post birth* (geometric mean, 95% CI) | 28.0 (27.8, 28.2) (n = 197) | 28.1 (27.9, 28.3) (n = 194) | 1.00 (0.99, 1.01) | 0.69 |
| Number of weeks gestation (median, interquartile range) | 39.7 (38.7, 40.7) (n = 205) | 39.6 (38.7, 40.4) (n = 201) | −0.1 (−0.4, 0.1) | 0.31† |

|  |  |  | Differences in means (95% CI) |  |
|---|---|---|---|---|
| Birth weight of child (kg) (mean, 95% CI) | 3.6 (3.5, 3.7) (n = 205) | 3.5 (3.4, 3.6) (n = 202) | 0.1 (−0.1, 0.2) | 0.36 |
| Birth length of child (cm) (mean, 95% CI) | 51.3 (51.0, 51.7) (n = 205) | 51.2 (50.8, 51.5) (n = 199) | 0.2 (−0.3, 0.7) | 0.48 |
| Ponderal index of child (mean, 95% CI) | 25.9 (25.5, 26.2) (n = 204) | 25.7 (25.4, 26.1) (n = 199) | 0.1 (−0.4, 0.7) | 0.59 |
| Head circumference of child (cm) (mean, 95% CI) | 35.3 (35.1, 35.6) (n = 205) | 35.4 (35.2, 35.6) (n = 201) | −0.1 (−0.4, 0.2) | 0.67 |

|  |  |  | RR (95% CI) |  |
|---|---|---|---|---|
| Macrosomia (≥4000 grams) | 22.4% (46/205) | 15.8% (32/202) | 1.41 (0.94, 2.12) | 0.10 |
| Premature (<37 weeks gestation) | 7.8% (16/205) | 4.0% (8/201) | 1.96 (0.86, 4.48) | 0.10 |
| Caesarean delivery | 27.7% (57/206) | 25.4% (51/201) | 1.09 (0.79, 1.51) | 0.60 |
| Admission to NICU | 11.3% (23/203) | 11.0% (22/201) | 1.04 (0.60, 1.80) | 0.90 |
| Apgar score ≥7 at 5 minutes | 98.5% (200/203) | 98.0% (198/202) | *1.51 (1.01, 2.27) | 0.04 |

NICU, Neonatal intensive care unit

*Analysis of covariance on logged values, adjusted for logged baseline measures, geometric means are fitted for the baseline geometric mean †Wilcoxon Rank Sum test ‡Odds ratio of having a higher Apgar score, Apgar scores grouped 0-3, 4-6, 7, 8, 9, 10. Ordinal logistic regression.

GDM in the mother, defined according to the IADPSG recommendations, was associated with higher maternal weight (p=0.0002), waist circumference (p<0.0001) and BMI (p<0.0001) post birth but was not associated with any infant anthropometric measures, gestation, caesarean delivery, NICU admission or Apgar score at five minutes (data not shown).

DISCUSSION

As far as the applicant is aware, this is the first study to report a role for probiotics in preventing GDM among women not selected on the basis of risk for GDM. The applicant's data suggest that the probiotic HN001 at a dose of $6 \times 10^9$ cfu/day may lower the rate of GDM from 13.8% to 8.2%, a 40% reduction using the IADPSG guidelines[6] or a 68% reduction from 6.5% to 2.1% using the NZ guidelines.

This study showed that the HN001 effect was stronger using the higher NZ glucose thresholds than the IADPSG thresholds to define GDM, suggesting that the effect is greater in preventing more severe GDM.

The gut microbiota is profoundly altered during the three trimesters of pregnancy towards a less diverse state, with the most depleted microbial richness found in women with GDM[9]. In contrast to obesity related gut microbiota, the last trimester gut microbiota has been associated with greater amounts of energy lost in stool compared to the first trimester, indicating that the impact of gut microbiota alterations during pregnancy on host adiposity and host glucose metabolism are not necessarily identical[9]. Without wishing to be bound to any theory, the applicants believe that HN001 supplementation altered the composition and function of the gut microbiota in favour of improved insulin sensitivity and inflammation to the host, which reduced the propensity to GDM.

The lack of any deleterious effect on birth outcomes supports HN001 as a safe intervention to take from early pregnancy (14-16 weeks gestation), which may also be beneficial to the infant, as reflected by the Apgar score. These findings are important given the small amount of data available on effects of early pregnancy probiotic interventions.

Promoting good health in pregnancy through weight control programs or diet has been largely ineffective partly due to poor adherence with the interventions. This study provides evidence that *L. rhamnosus* HN001 is an effective intervention for reducing the prevalence of GDM, particularly in older mothers and those with a history of GDM.

INDUSTRIAL APPLICABILITY

This invention relates to the use of probiotic bacteria, particularly *Lactobacillus rhamnosus* HN001 or derivatives thereof, and in particular in the treatment or prevention of GDM. Methods for using the bacteria and compositions comprising the bacteria are also provided

REFERENCES

1. Ministry of Health (2014) Screening, diagnosis and management of gestational diabetes in New Zealand: A clinical practice guideline. Ministry of Health, Wellington.
2. American Committee of Obstetricians and Gynecologists Committee Opinion number 549 (January 2013) Obesity in pregnancy. Obstet Gynecol 121: 213-217.
3. Kim S Y, England L, Wilson H G, Bish C, Satten G A, Dietz P (2010) Percentage of gestational diabetes mellitus attributable to overweight and obesity. Am J Pub Health 100: 1047-1052.
4. Ben-Haroush A, Yogev Y, Hod M (2004) Epidemiology of gestational diabetes mellitus and its association with Type 2 diabetes. Diabet Med 21: 103-113.
5. Kim C, Newton K M, Knopp R H (2002) Gestational diabetes and the incidence of type 2 diabetes. Diabetes Care 25: 1862-1868.
6. International Association of Diabetes and Pregnancy Study Groups Consensus Panel (2010) International Association of Diabetes and Pregnancy Study Groups Recommendations on the diagnosis and classification of hyperglycemia in pregnancy. Diabetes Care 33: 676-682.
7. Luoto R, Laitinen K, Nermes M, Isolauri E (2010) Impact of maternal probiotic-supplemented dietary counseling on pregnancy outcome and prenatal and postnatal growth: a double-blind, placebo-controlled study. Br J Nutr 103: 1792-1799.
8. Wickens K, Black P N, Stanley T V, et al. (2008) A differential effect of 2 probiotics in the prevention of eczema and atopy: A double-blind, randomized, placebo-controlled trial. J Allergy Clin Imunol 122: 788-794.
9. Koren O, Goodrich J K, Tyler C C, et al. (2012) Host remodelling of the gut microbiome and metabolic changes during pregnancy. Cell 150: 470-480.
10. Barrett H L, Dekker Nitert M, Conwell L S, Callaway L K. Probiotics for preventing gestational diabetes. Cochrane Database Syst Rev. 2014; Art. No.: CD009951. DOI: 10.1002/14651858.CD009951.
11. International Association of Diabetes and Pregnancy Study Groups Consensus Panel. International Association of Diabetes and Pregnancy Study Groups recommendations on the diagnosis and classification of hyperglycemia in pregnancy. Diabetes Care. 2010; 33:676-82.
12. Poston L, Harthoorn L F, Van Der Beek E M. Obesity in pregnancy: Implications for the mother and lifelong health of the child. A consensus statement. Pediatr Res. 2011; 69:175-80.
13. Vohr B R, Boney C M. Gestational diabetes: the forerunner for the development of maternal and childhood obesity and metabolic syndrome? J Matern Neonatal Med. 2008; 21:149-57.
14. Chandler-Laney P C, Bush N C, Granger W M, Rouse D J, Mancuso M S, Gower B A. Overweight status and intrauterine exposure to gestational diabetes are associated with children's metabolic health. Pediatr Obes. 2011; 7:44-52.
15. Nitert M D, Barrett H L, Foxcroft K, Tremellen A, Wilkinson S, Lingwood B, et al. SPRING: an RCT study of probiotics in the prevention of gestational diabetes mellitus in overweight and obese women. BMC Pregnancy Childbirth. 2013; 13:50.

The invention claimed is:

1. A method of treating or attenuating gestational diabetes mellitus (GDM), one or more symptoms of GDM, or at least one sequela of GDM in an adult pregnant subject in need thereof, or in a foetal, neonatal, infant or child subject in need thereof, the method comprising oral administration of an effective amount of the isolated *Lactobacillus rhamnosus* HN001 having the deposit number NM97/09514 to the adult pregnant subject or to a birth mother of the foetal, neonatal, infant or child subject during gestation, wherein a mean fasting blood glucose in the adult pregnant subject or the birth mother of the foetal, neonatal, infant or child subject is lowered to less than 4.35 mmol/l.

2. The method of claim 1, wherein the adult pregnant subject or the birth mother of the foetal, neonatal, infant or child subject has a history of previous GDM.

3. The method of claim 1, wherein
the subject is a foetal subject and the *L. rhamnosus* HN001 is orally administered to the foetal subject's birth mother, or
the subject is a neonatal, infant, or child subject and the *L. rhamnosus* HN001 is orally administered to the neonatal, infant, or child subject's birth mother.

4. The method of claim 1, wherein the adult pregnant subject or the birth mother of the foetal, neonatal, infant or child subject has a body mass index (BMI) of less than 30 kg/m$^2$.

5. The method of claim 1, wherein the *L. rhamnosus* HN001 is administered in a composition comprising a physiologically acceptable diluent, adjuvant, carrier or excipient.

6. The method of claim 1, wherein the *L. rhamnosus* HN001 is administered in a composition comprising a food.

7. The method of claim 6, wherein the food is selected from cultured milk, yoghurt, cheese, milk drink and milk powder.

8. The method of claim 5, wherein the *L. rhamnosus* HN001 is administered in a pharmaceutical composition comprising a pharmaceutically acceptable diluent, adjuvant, carrier or excipient.

9. The method of claim 1, wherein the *L. rhamnosus* HN001 is administered in at least one of a maternal formula, a maternal supplement, and a dietetic product.

10. The method of claim 1, wherein the *L. rhamnosus* HN001 is in a reproductively viable form.

11. The method of claim 1, wherein the *L. rhamnosus* HN001 is killed, lysed, fractionated or attenuated.

12. The method of claim 1, wherein the adult pregnant subject, or the birth mother of the foetal, neonatal, infant or child subject, has previously suffered GDM.

13. The method of claim 1, wherein the adult pregnant subject, or the birth mother of the foetal, neonatal, infant or child subject, is over the age of 35 years.

14. The method of claim 1, wherein the adult pregnant subject, or the birth mother of the foetal, neonatal, infant or child subject, has previously been pregnant.

15. The method of claim 1, wherein the administration of the *L. rhamnosus* HN001 begins after the first trimester of pregnancy.

16. The method of claim 1, wherein
(a) the administration of the *L. rhamnosus* HN001 begins between 14 to 16 weeks gestation,
(b) the administration of the *L. rhamnosus* HN001 occurs from 14 to 16 weeks of gestation until delivery, or
(c) the administration of the *L. rhamnosus* HN001 occurs from 14 to 16 weeks of gestation to 6 months postpartum.

17. The method of claim 1, wherein the method comprises simultaneous or sequential administration of the *L. rhamnosus* HN001 with a prebiotic.

18. The method of claim 17, wherein the prebiotic comprises fructooligosaccharides, galactooligosaccharides, human milk oligosaccharides, or a combination thereof.

* * * * *

UNITED STATES PATENT AND TRADEMARK OFFICE
CERTIFICATE OF CORRECTION

PATENT NO. : 11,395,839 B2  
APPLICATION NO. : 16/472071  
DATED : July 26, 2022  
INVENTOR(S) : Kristin Lee Wickens Page 1 of 1

It is certified that error appears in the above-identified patent and that said Letters Patent is hereby corrected as shown below:

On the Title Page

Column 2 (item (56) Other Publications), Line 43, delete "Imunol" and insert -- Immunol --.

Page 2, Column 2 (item (56) Other Publications), Line 2, delete "Microbiotia" and insert -- Microbiota --.

In the Specification

Column 4, Line 12 (approx.), delete "trial" and insert -- trial. --.

Column 6, Line 21, delete "Genebank" and insert -- Genbank --.

Column 10, Line 54, delete "stablisers," and insert -- stabilizers, --.

Column 16, Line 12-13, delete "probioitics," and insert -- probiotics, --.

Column 18, Line 52, delete "hayfever" and insert -- hay fever --.

Column 23, Line 47 (approx.), delete "HbA1$_c$," and insert -- HbA1$_c$ --.

Column 25-26, Line 50, delete "*1.51" and insert -- ‡1.51 --.

Column 27, Line 57, delete "provided" and insert -- provided. --.

Column 28, Line 24, delete "Imunol" and insert -- Immunol --.

In the Claims

Column 28, Line 67, Claim 1, delete "mmol/I." and insert -- mmol/l. --.

Signed and Sealed this  
First Day of November, 2022

Katherine Kelly Vidal  
*Director of the United States Patent and Trademark Office*